United States Patent
Cam et al.

(10) Patent No.: US 9,351,859 B2
(45) Date of Patent: May 31, 2016

(54) VASCULAR REMODELING DEVICE

(75) Inventors: Anh Cam, Carlsbad, CA (US); Michael Louis Losordo, San Juan Capistrano, CA (US); Jianlu Ma, Irvine, CA (US); Luong Nguyen, Irvine, CA (US); Sanjay Shrivastava, Irvine, CA (US); John Wainwright, Mission Viejo, CA (US); Xiaoling Zhao, Irvine, CA (US)

(73) Assignee: Covidien LP, Mansfield, MA (US)

( * ) Notice: Subject to any disclaimer, the term of this patent is extended or adjusted under 35 U.S.C. 154(b) by 1184 days.

(21) Appl. No.: 13/312,887

(22) Filed: Dec. 6, 2011

(65) Prior Publication Data
US 2012/0143317 A1 Jun. 7, 2012

Related U.S. Application Data

(60) Provisional application No. 61/420,275, filed on Dec. 6, 2010, provisional application No. 61/448,506, filed on Mar. 2, 2011.

(51) Int. Cl.
*A61F 2/06* (2013.01)
*A61F 2/90* (2013.01)
(Continued)

(52) U.S. Cl.
CPC .............. *A61F 2/90* (2013.01); *A61B 17/1214* (2013.01); *A61B 17/12118* (2013.01);
(Continued)

(58) Field of Classification Search
CPC ............ A61B 17/12022; A61B 17/12172; A61B 17/12113; A61B 17/12118; A61B 2017/00867; A61F 2/90; A61F 2/95; A61F 17/1214; A61F 17/12118; A61F 17/12172
See application file for complete search history.

(56) References Cited

U.S. PATENT DOCUMENTS

| 4,921,484 A | 5/1990 | Hillstead |
| 5,122,136 A | 6/1992 | Guglielmi et al. |

(Continued)

FOREIGN PATENT DOCUMENTS

| CN | 1556689 A | 12/2004 |
| CN | 101415449 A | 4/2009 |

(Continued)

OTHER PUBLICATIONS

Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.
(Continued)

*Primary Examiner* — Tuan V Nguyen
*Assistant Examiner* — Kevin Everage
(74) *Attorney, Agent, or Firm* — Mark J. Kertz, Esq.

(57) ABSTRACT

Described herein are vascular remodeling devices that include a proximal section, an intermediate section, and a distal section. During deployment, the proximal section can expand from a compressed delivery state to an expanded state and anchors the device in an afferent vessel of a bifurcation. The distal section expands from the compressed delivery state to an expanded state that may be substantially planar, approximately semi-spherical, umbrella shaped, or reverse umbrella shaped. The distal section is positioned in a bifurcation junction across the neck of an aneurysm or within an aneurysm. The intermediate section allows perfusion to efferent vessels. Before or after the device is in position, embolic material may be used to treat the aneurysm. The distal section can act as a scaffolding to prevent herniation of the embolic material. The device can be used for clot retrieval with integral distal embolic protection.

23 Claims, 18 Drawing Sheets

(51) Int. Cl.
*A61B 17/12* (2006.01)
*A61F 2/95* (2013.01)
*A61F 2/82* (2013.01)

(52) U.S. Cl.
CPC .......... *A61B 17/12172* (2013.01); *A61F 2/95* (2013.01); *A61F 2002/823* (2013.01); *A61F 2220/005* (2013.01); *A61F 2220/0058* (2013.01); *A61F 2230/0034* (2013.01); *A61F 2230/0054* (2013.01)

(56) References Cited

U.S. PATENT DOCUMENTS

| | | | |
|---|---|---|---|
| 5,624,461 A | 4/1997 | Mariant | |
| 5,645,558 A | 7/1997 | Horton | |
| 5,690,671 A | 11/1997 | McGurk et al. | |
| 5,725,552 A | 3/1998 | Kotula et al. | |
| 5,728,906 A | 3/1998 | Eguchi et al. | |
| 5,733,294 A | 3/1998 | Forber et al. | |
| 5,879,366 A | 3/1999 | Shaw et al. | |
| 5,911,731 A | 6/1999 | Pham et al. | |
| 5,916,235 A | 6/1999 | Guglielmi | |
| 5,925,060 A | 7/1999 | Forber | |
| 5,928,260 A | 7/1999 | Chin et al. | |
| 5,935,148 A | 8/1999 | Villar et al. | |
| 5,951,599 A | 9/1999 | McCrory | |
| 5,957,948 A | 9/1999 | Mariant | |
| 6,024,756 A | 2/2000 | Huebsch et al. | |
| 6,036,720 A | 3/2000 | Abrams et al. | |
| 6,063,070 A | 5/2000 | Eder | |
| 6,063,104 A | 5/2000 | Villar et al. | |
| 6,086,577 A | 7/2000 | Ken et al. | |
| 6,096,073 A | 8/2000 | Webster et al. | |
| 6,168,615 B1 | 1/2001 | Ken et al. | |
| 6,168,622 B1 | 1/2001 | Mazzocchi | |
| 6,221,086 B1 | 4/2001 | Forber | |
| 6,261,305 B1 | 7/2001 | Marotta et al. | |
| 6,306,141 B1 | 10/2001 | Jervis | |
| 6,309,367 B1 | 10/2001 | Boock | |
| 6,322,576 B1 | 11/2001 | Wallace et al. | |
| 6,325,820 B1 | 12/2001 | Khosravi et al. | |
| 6,331,184 B1 | 12/2001 | Abrams | |
| 6,344,048 B1 | 2/2002 | Chin et al. | |
| 6,346,117 B1 | 2/2002 | Greenhalgh | |
| 6,350,270 B1 | 2/2002 | Roue | |
| 6,375,668 B1 | 4/2002 | Gifford et al. | |
| 6,428,558 B1 | 8/2002 | Jones et al. | |
| 6,454,780 B1 | 9/2002 | Wallace | |
| 6,506,204 B2 | 1/2003 | Mazzocchi | |
| 6,517,558 B2 | 2/2003 | Gittings et al. | |
| 6,551,303 B1 | 4/2003 | Van Tassel et al. | |
| 6,582,463 B1 | 6/2003 | Mowry et al. | |
| 6,585,748 B1 | 7/2003 | Jeffree | |
| 6,585,756 B1 | 7/2003 | Stecker | |
| 6,589,256 B2 | 7/2003 | Forber | |
| 6,589,265 B1 | 7/2003 | Palmer et al. | |
| 6,605,102 B1 | 8/2003 | Mazzocchi et al. | |
| 6,605,111 B2 | 8/2003 | Bose et al. | |
| 6,635,068 B1 | 10/2003 | Dubrul et al. | |
| 6,635,069 B1 | 10/2003 | Teoh et al. | |
| 6,666,883 B1 | 12/2003 | Seguin et al. | |
| 6,669,717 B2 | 12/2003 | Marotta et al. | |
| 6,669,721 B1 | 12/2003 | Bose et al. | |
| 6,676,696 B1 | 1/2004 | Marotta et al. | |
| 6,695,876 B1 | 2/2004 | Marotta et al. | |
| 6,712,835 B2 | 3/2004 | Mazzocchi et al. | |
| 6,730,108 B2 | 5/2004 | Van Tassel et al. | |
| 6,746,468 B1 | 6/2004 | Sepetka et al. | |
| 6,746,890 B2 | 6/2004 | Gupta et al. | |
| 6,780,196 B2 | 8/2004 | Chin et al. | |
| 6,797,083 B2 | 9/2004 | Peterson | |
| 6,802,851 B2 | 10/2004 | Jones et al. | |
| 6,860,893 B2 | 3/2005 | Wallace et al. | |
| 6,949,103 B2 | 9/2005 | Mazzocchi et al. | |
| 6,953,472 B2 | 10/2005 | Palmer et al. | |
| 6,989,019 B2 | 1/2006 | Mazzocchi et al. | |
| 6,994,717 B2 | 2/2006 | Konya et al. | |
| 7,029,487 B2 | 4/2006 | Greene, Jr. et al. | |
| 7,033,375 B2 | 4/2006 | Mazzocchi et al. | |
| 7,048,752 B2 | 5/2006 | Mazzocchi et al. | |
| 7,128,736 B1 | 10/2006 | Abrams et al. | |
| 7,195,636 B2 | 3/2007 | Avellanet et al. | |
| 7,229,461 B2 | 6/2007 | Chin et al. | |
| 7,232,461 B2 | 6/2007 | Ramer | |
| 7,331,980 B2 | 2/2008 | Dubrul et al. | |
| 7,367,985 B2 | 5/2008 | Mazzocchi et al. | |
| 7,367,986 B2 | 5/2008 | Mazzocchi et al. | |
| 7,371,250 B2 | 5/2008 | Mazzocchi et al. | |
| 7,404,820 B2 | 7/2008 | Mazzocchi et al. | |
| 7,410,482 B2 | 8/2008 | Murphy et al. | |
| 7,410,492 B2 | 8/2008 | Mazzocchi et al. | |
| 7,413,622 B2 | 8/2008 | Peterson | |
| 7,442,200 B2 | 10/2008 | Mazzocchi et al. | |
| 7,485,088 B2 | 2/2009 | Murphy et al. | |
| 7,556,635 B2 | 7/2009 | Mazzocchi et al. | |
| 7,566,338 B2 | 7/2009 | Mazzocchi et al. | |
| 7,569,066 B2 | 8/2009 | Gerberding et al. | |
| 7,572,273 B2 | 8/2009 | Mazzocchi et al. | |
| 7,582,111 B2 | 9/2009 | Krolik et al. | |
| 7,621,928 B2 | 11/2009 | Thramann et al. | |
| 7,670,355 B2 | 3/2010 | Mazzocchi et al. | |
| 7,670,356 B2 | 3/2010 | Mazzocchi et al. | |
| 7,678,130 B2 | 3/2010 | Mazzocchi et al. | |
| 7,744,652 B2 | 6/2010 | Morsi | |
| 7,763,011 B2 | 7/2010 | Ortiz et al. | |
| 7,763,065 B2 | 7/2010 | Schmid et al. | |
| 7,828,815 B2 | 11/2010 | Mazzocchi et al. | |
| 7,828,816 B2 | 11/2010 | Mazzocchi et al. | |
| 7,833,259 B2 | 11/2010 | Boatman | |
| 7,862,604 B1 | 1/2011 | Marcade et al. | |
| 7,887,576 B2 | 2/2011 | Bahler et al. | |
| 7,914,567 B2 | 3/2011 | Paucnik et al. | |
| 7,922,732 B2 | 4/2011 | Mazzocchi et al. | |
| 7,951,192 B2 | 5/2011 | Yadin et al. | |
| 8,388,650 B2 | 3/2013 | Gerberding et al. | |
| 2001/0007946 A1 | 7/2001 | Lenker et al. | |
| 2003/0028209 A1 | 2/2003 | Teoh et al. | |
| 2003/0171739 A1 | 9/2003 | Murphy et al. | |
| 2003/0195553 A1 | 10/2003 | Wallace et al. | |
| 2004/0111112 A1 | 6/2004 | Hoffmann | |
| 2004/0111121 A1 | 6/2004 | Brown et al. | |
| 2004/0172056 A1 | 9/2004 | Guterman et al. | |
| 2004/0186562 A1 | 9/2004 | Cox | |
| 2004/0193206 A1 | 9/2004 | Gerberding et al. | |
| 2004/0249408 A1 | 12/2004 | Murphy et al. | |
| 2005/0033409 A1 | 2/2005 | Burke et al. | |
| 2005/0096728 A1* | 5/2005 | Ramer ............ A61B 17/12022 623/1.15 |
| 2006/0052816 A1 | 3/2006 | Bates et al. | |
| 2006/0058864 A1 | 3/2006 | Schaeffer et al. | |
| 2006/0064151 A1 | 3/2006 | Guterman et al. | |
| 2006/0190070 A1 | 8/2006 | Dieck et al. | |
| 2006/0264905 A1 | 11/2006 | Eskridge et al. | |
| 2006/0264907 A1 | 11/2006 | Eskridge et al. | |
| 2007/0016243 A1 | 1/2007 | Ramaiah et al. | |
| 2007/0088387 A1 | 4/2007 | Eskridge et al. | |
| 2007/0106311 A1 | 5/2007 | Wallace et al. | |
| 2007/0173928 A1 | 7/2007 | Morsi | |
| 2007/0191884 A1 | 8/2007 | Eskridge et al. | |
| 2007/0198075 A1 | 8/2007 | Levy | |
| 2007/0203567 A1 | 8/2007 | Levy | |
| 2007/0225794 A1 | 9/2007 | Thramann et al. | |
| 2007/0225798 A1 | 9/2007 | Gregorich | |
| 2007/0265656 A1 | 11/2007 | Amplatz et al. | |
| 2007/0270902 A1* | 11/2007 | Slazas ............ A61B 17/12022 606/200 |
| 2008/0058856 A1 | 3/2008 | Ramaiah et al. | |
| 2008/0109063 A1 | 5/2008 | Hancock et al. | |
| 2008/0114436 A1 | 5/2008 | Dieck et al. | |
| 2008/0114439 A1 | 5/2008 | Ramaiah et al. | |
| 2008/0125806 A1 | 5/2008 | Mazzocchi et al. | |
| 2008/0221600 A1 | 9/2008 | Dieck et al. | |
| 2009/0043371 A1 | 2/2009 | Fearnot | |
| 2009/0069806 A1 | 3/2009 | De La Mora Levy et al. | |

(56) References Cited

U.S. PATENT DOCUMENTS

| | | |
|---|---|---|
| 2009/0118811 A1 | 5/2009 | Moloney |
| 2009/0143851 A1 | 6/2009 | Paul, Jr. |
| 2009/0264914 A1 | 10/2009 | Riina et al. |
| 2009/0275974 A1 | 11/2009 | Marchand et al. |
| 2009/0287291 A1 | 11/2009 | Becking et al. |
| 2009/0287294 A1 | 11/2009 | Rosequeta et al. |
| 2010/0004726 A1 | 1/2010 | Hancock et al. |
| 2010/0004761 A1 | 1/2010 | Flanders et al. |
| 2010/0023105 A1 | 1/2010 | Levy et al. |
| 2010/0069948 A1 | 3/2010 | Veznedarogly et al. |
| 2010/0094335 A1 | 4/2010 | Gerberding et al. |
| 2011/0022149 A1 | 1/2011 | Cox et al. |
| 2011/0160757 A1 | 6/2011 | Ferrera et al. |
| 2011/0184452 A1 | 7/2011 | Huynh et al. |
| 2011/0184453 A1 | 7/2011 | Levy et al. |
| 2011/0245862 A1 | 10/2011 | Dieck et al. |
| 2012/0143237 A1 | 6/2012 | Cam et al. |
| 2012/0296362 A1 | 11/2012 | Cam et al. |
| 2012/0323160 A1 * | 12/2012 | Babkes .................. 604/9 |
| 2013/0204290 A1 | 8/2013 | Clarke et al. |
| 2013/0304109 A1 | 11/2013 | Abrams et al. |
| 2014/0058420 A1 | 2/2014 | Hannes et al. |

FOREIGN PATENT DOCUMENTS

| | | | |
|---|---|---|---|
| CN | 102137626 A | | 7/2011 |
| CN | 102361602 A | | 2/2012 |
| CN | 102740799 A | | 10/2012 |
| CN | 102762156 A | | 10/2012 |
| DE | 102008028308 A1 | | 4/2009 |
| EP | 1527753 A2 | | 5/2005 |
| WO | WO-97/26939 A1 | | 7/1997 |
| WO | WO-98/50102 A1 | | 11/1998 |
| WO | WO-99/05977 | | 2/1999 |
| WO | WO-01/93782 | | 12/2001 |
| WO | WO-02/00139 | | 1/2002 |
| WO | WO-2005/117718 | | 12/2005 |
| WO | WO-2006/034166 A2 | | 3/2006 |
| WO | WO-2006/119422 | | 11/2006 |
| WO | WO-2007/047851 | | 4/2007 |
| WO | WO-2008/022327 A2 | | 2/2008 |
| WO | WO-2008/151204 | | 12/2008 |
| WO | WO-2008/151205 A2 | | 12/2008 |
| WO | WO-2009/076515 | | 6/2009 |
| WO | WO-2009/135166 | | 11/2009 |
| WO | WO-2010/028314 | | 3/2010 |
| WO | WO-2010/030991 A1 | | 3/2010 |
| WO | WO-2012/078678 A1 | | 6/2012 |
| WO | WO-2012/154782 A1 | | 11/2012 |

OTHER PUBLICATIONS

U.S. Appl. No. 13/664,648, filed Oct. 31, 2012.

* cited by examiner

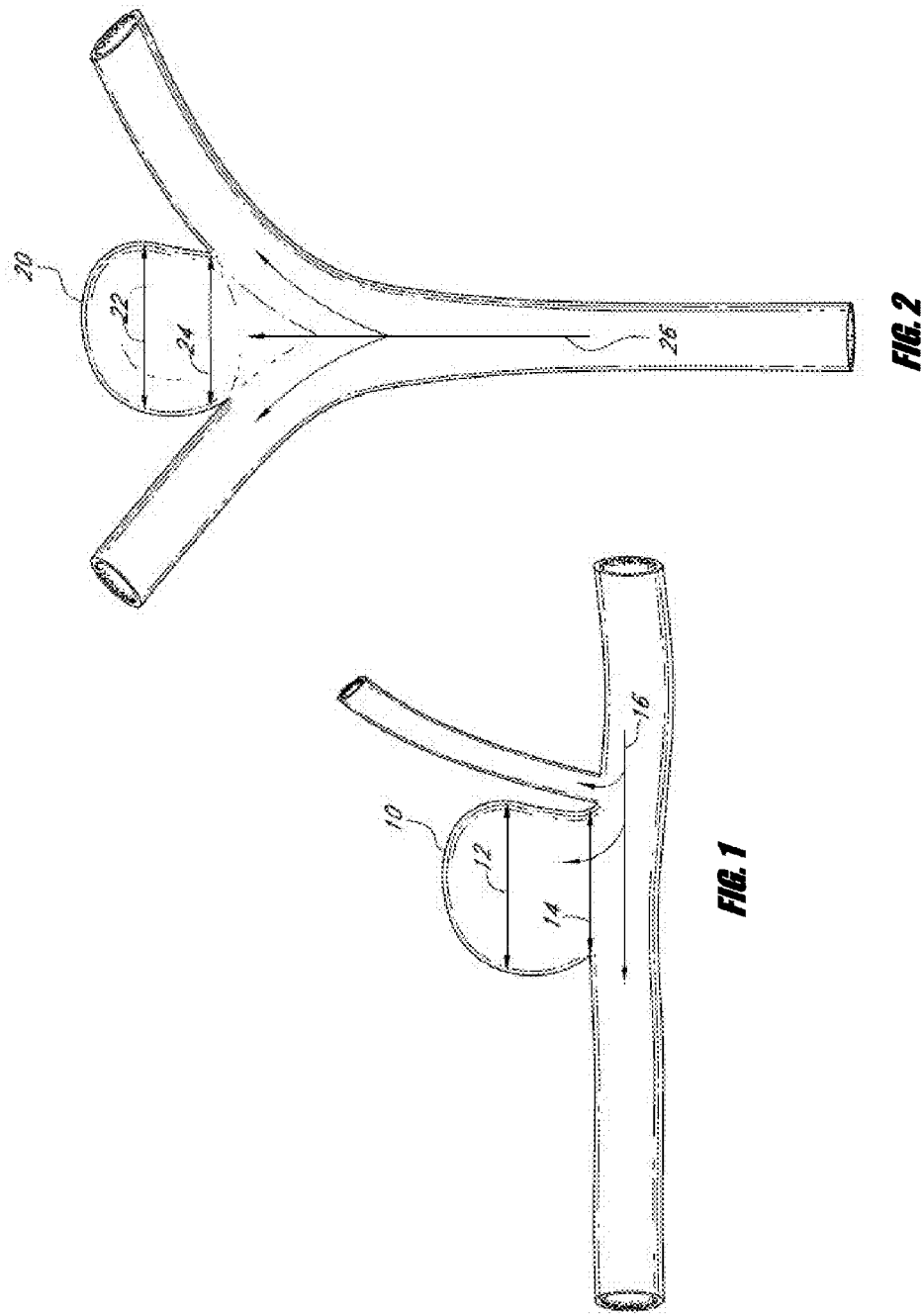

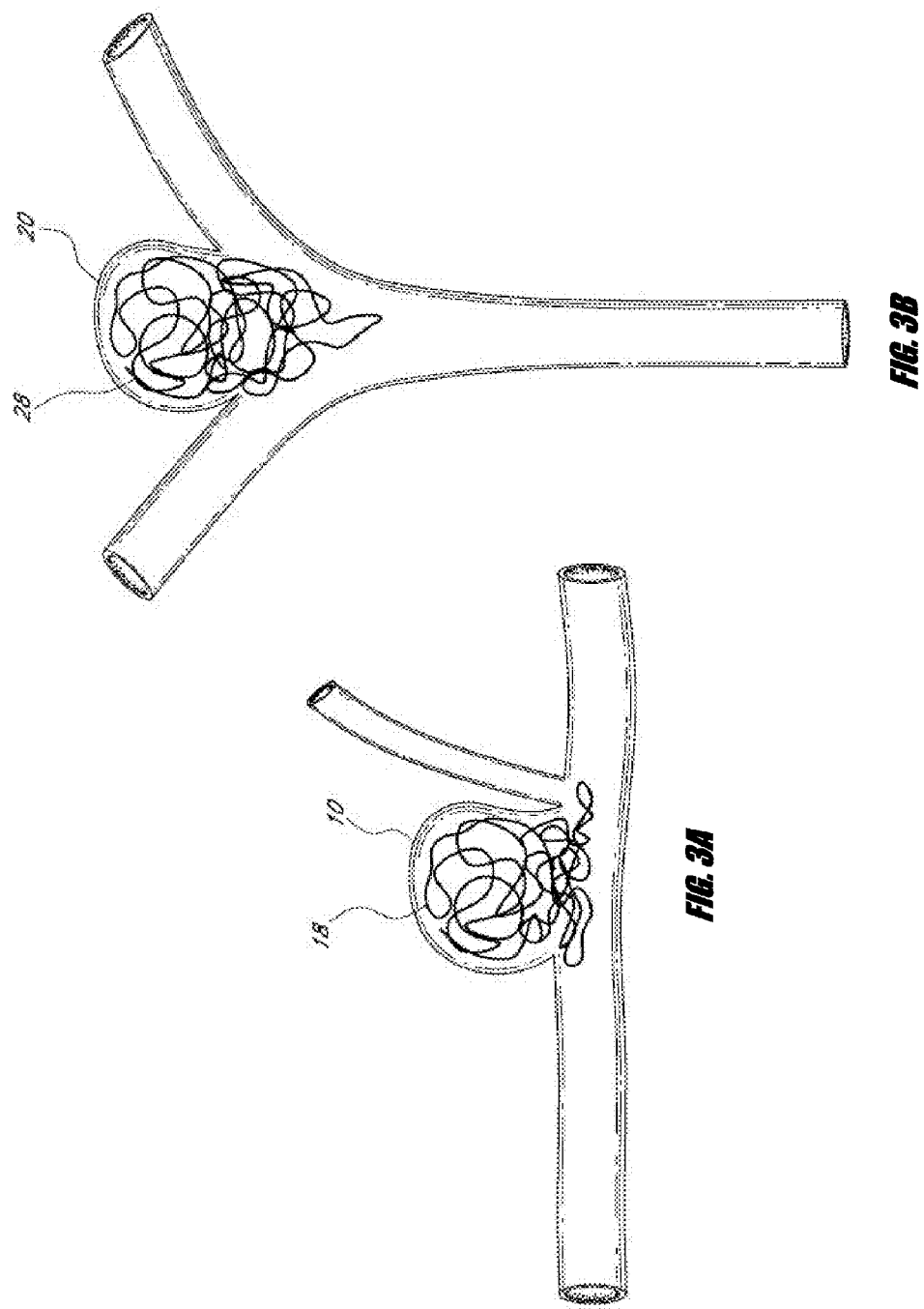

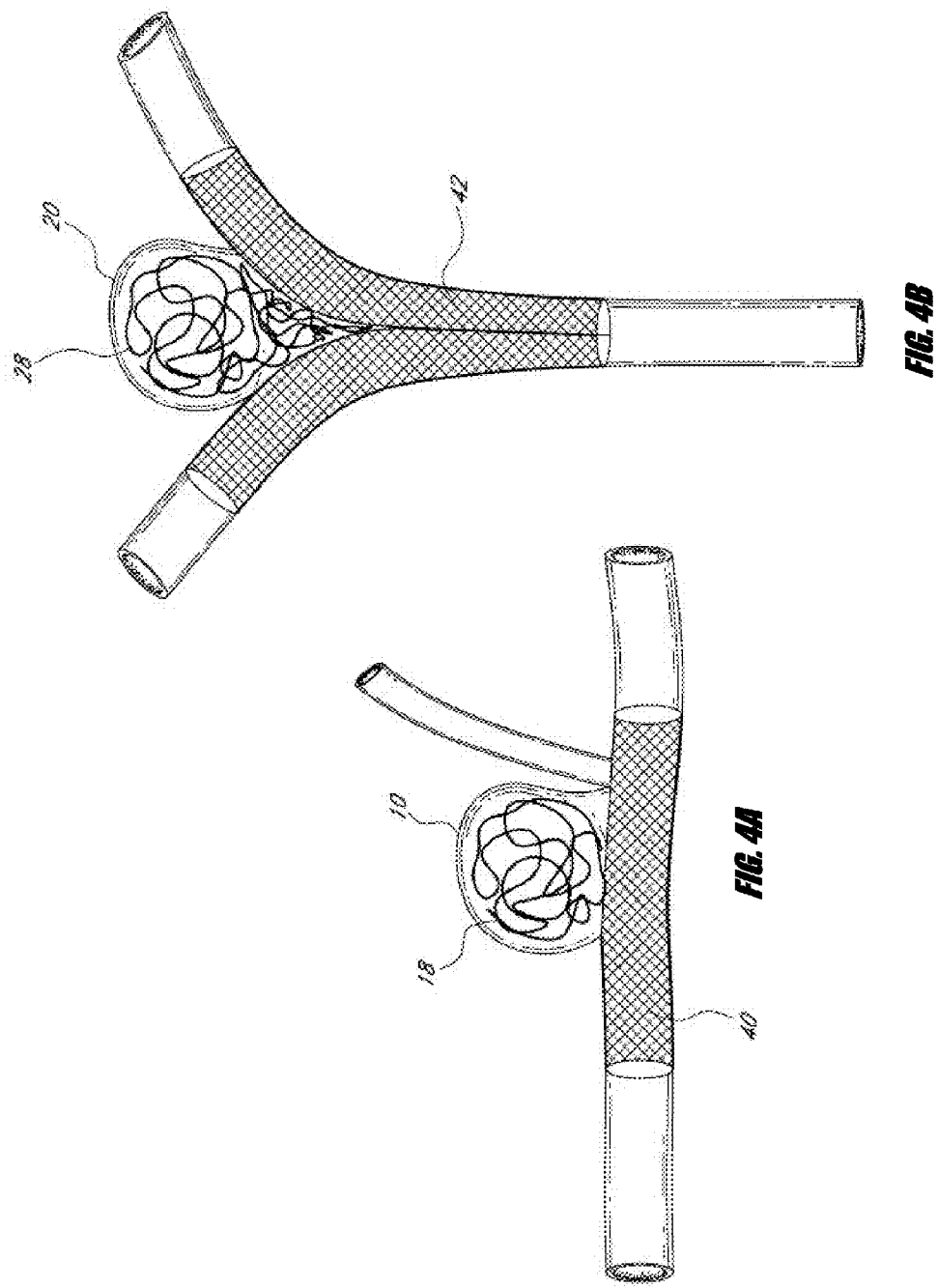

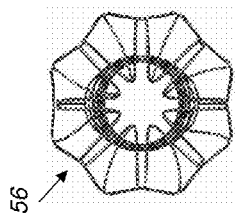 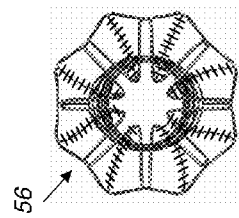 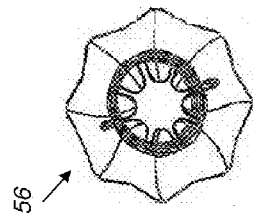
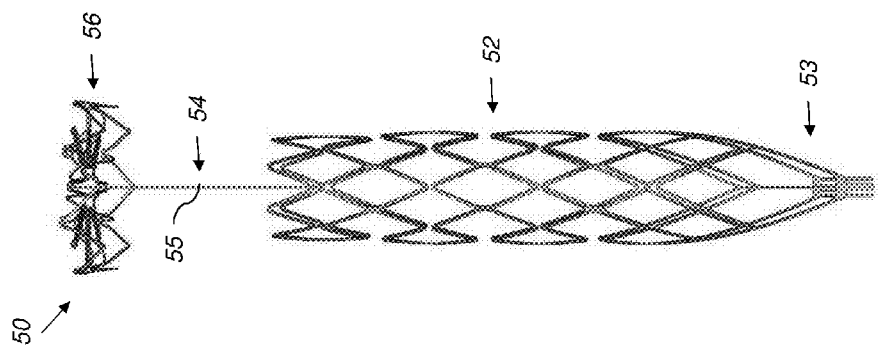
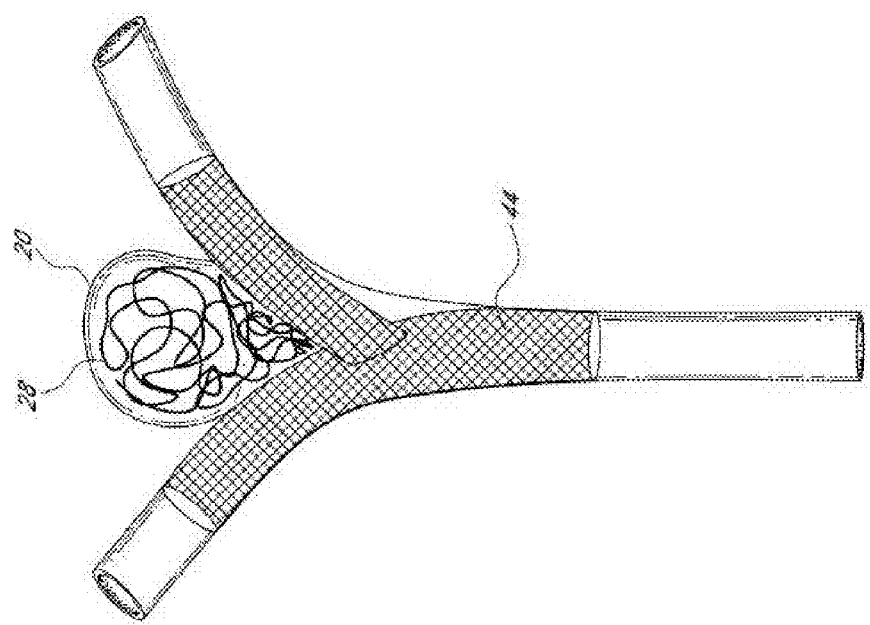

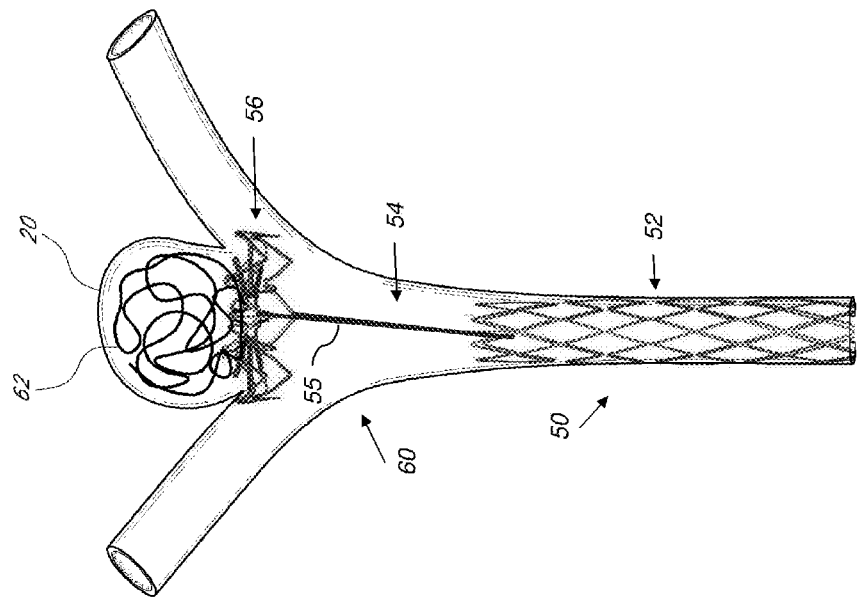
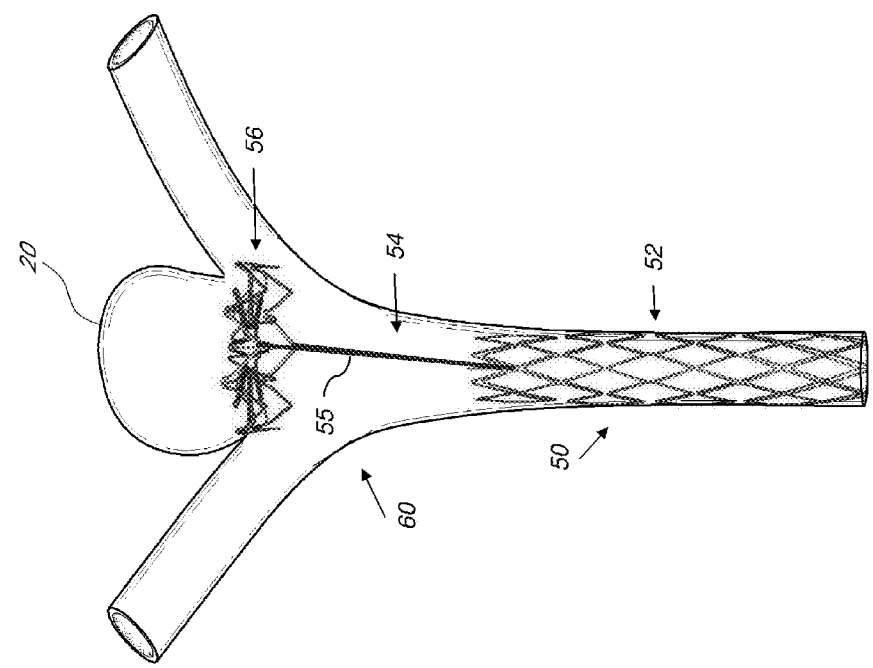

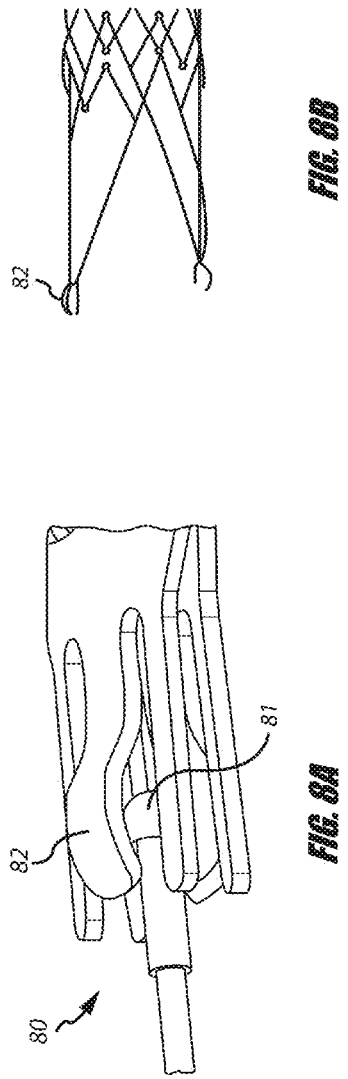
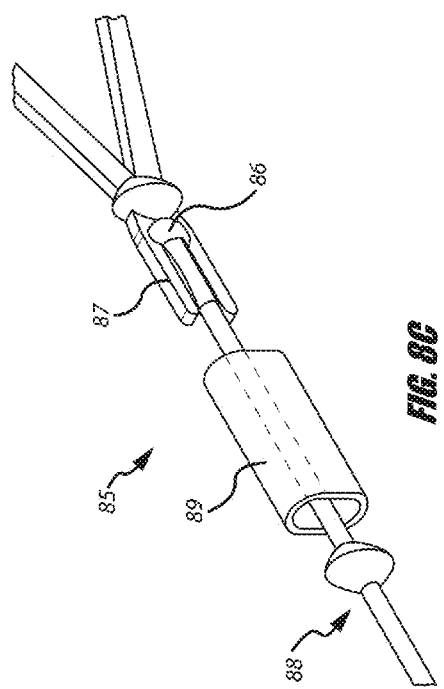

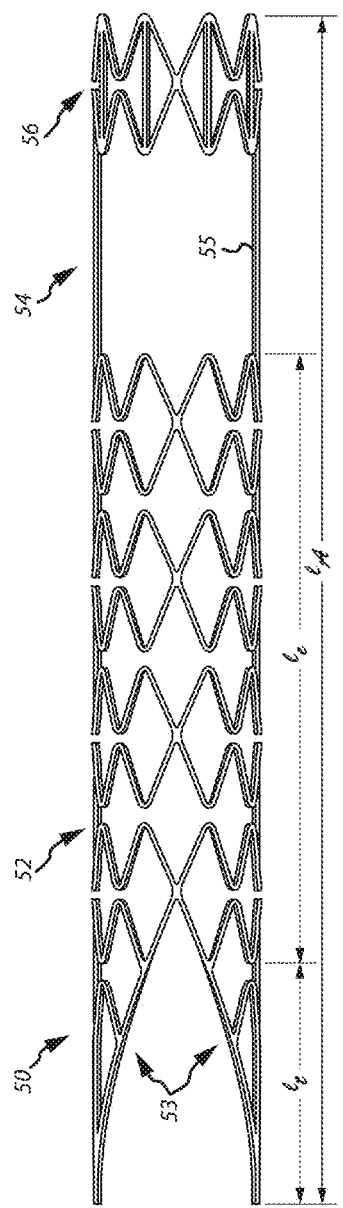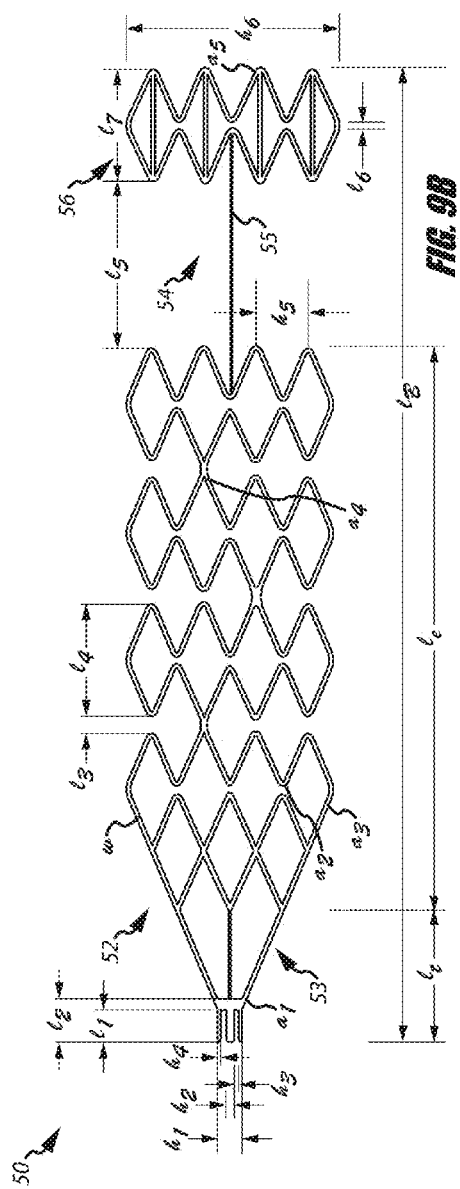
FIG. 9A
FIG. 9B

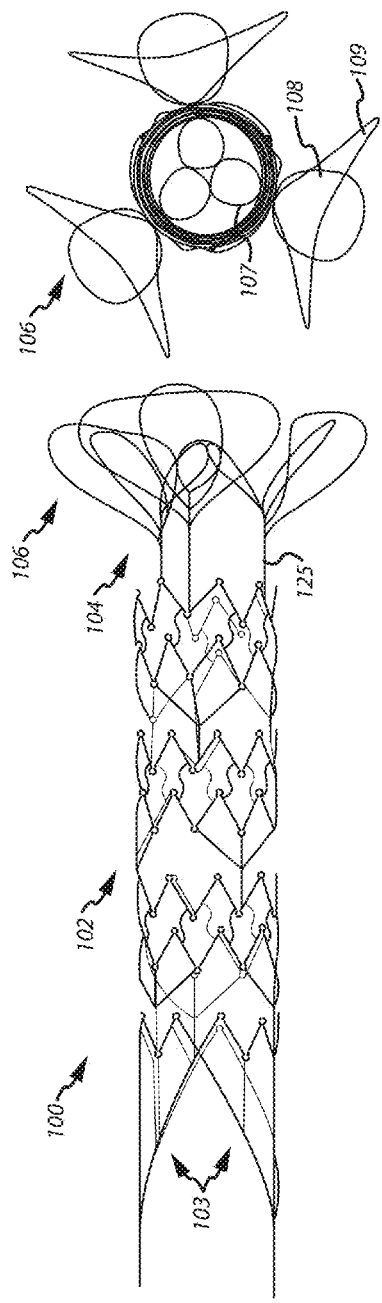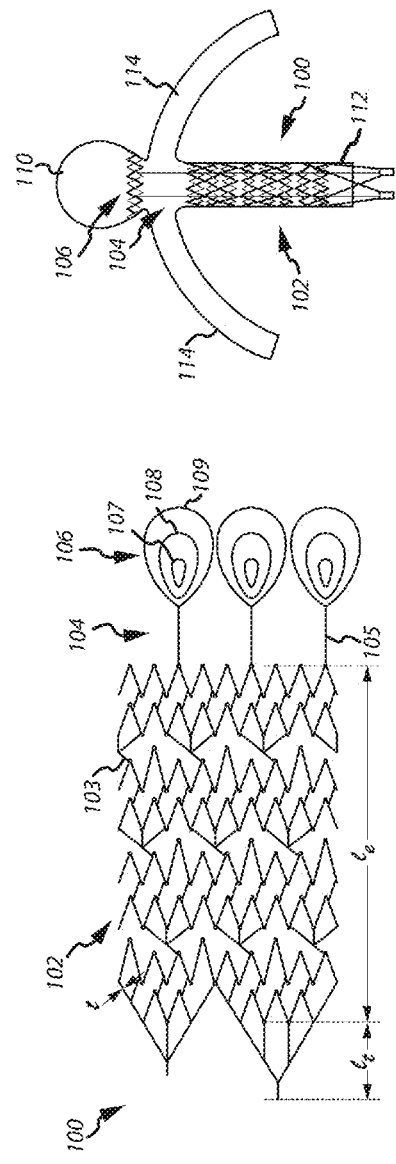

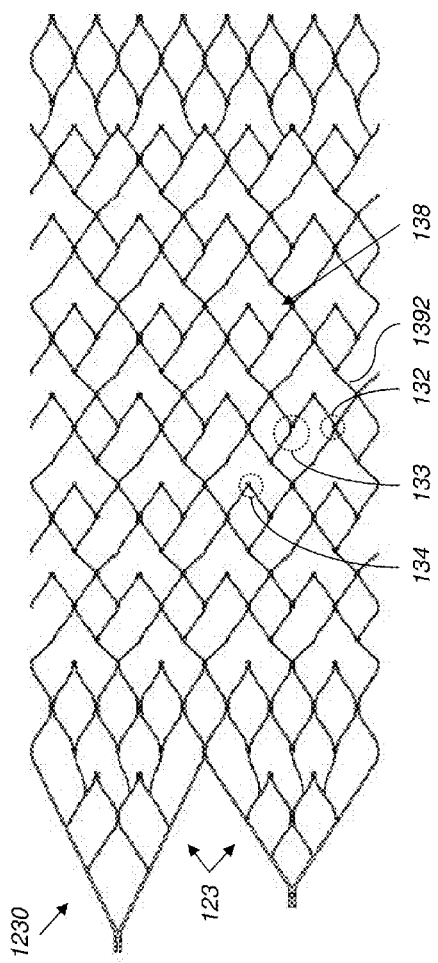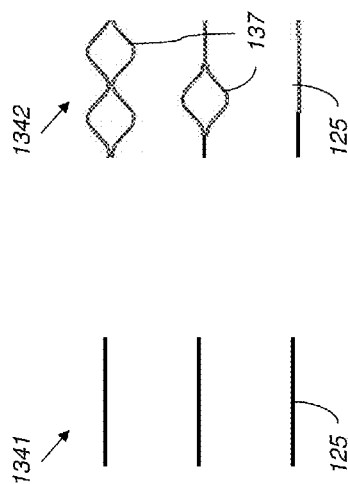

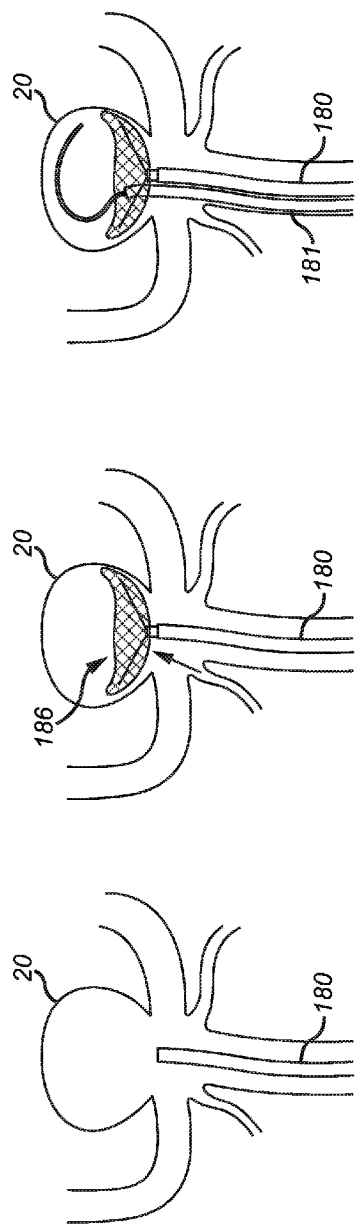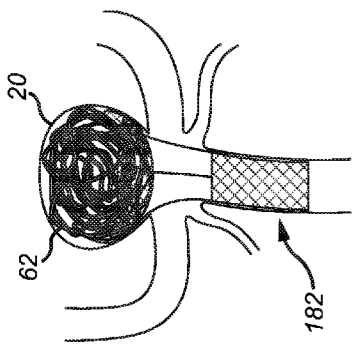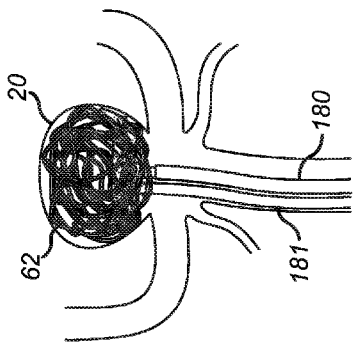

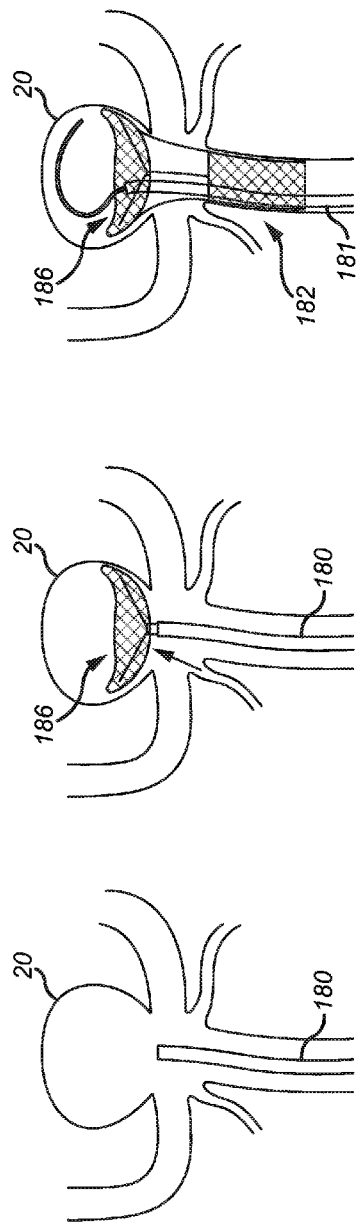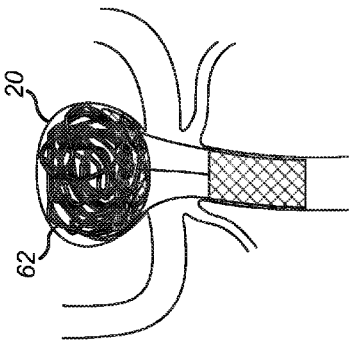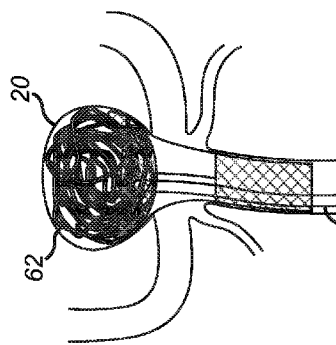

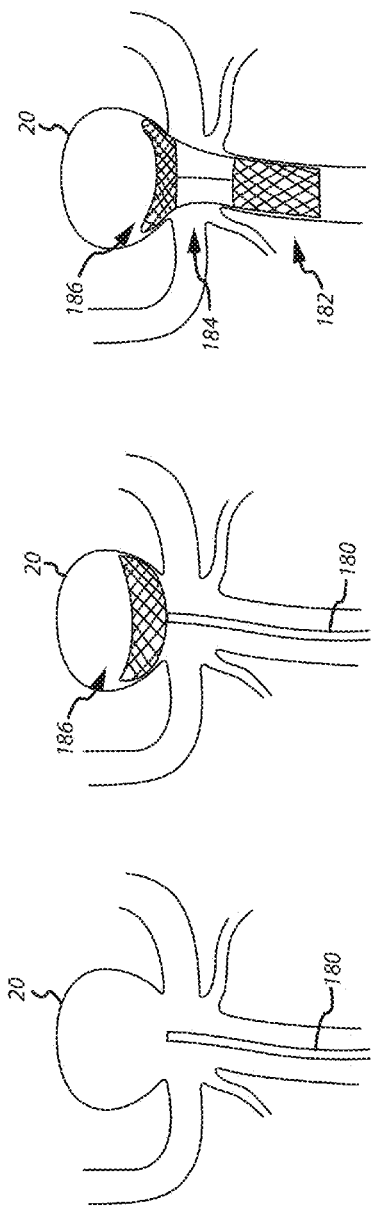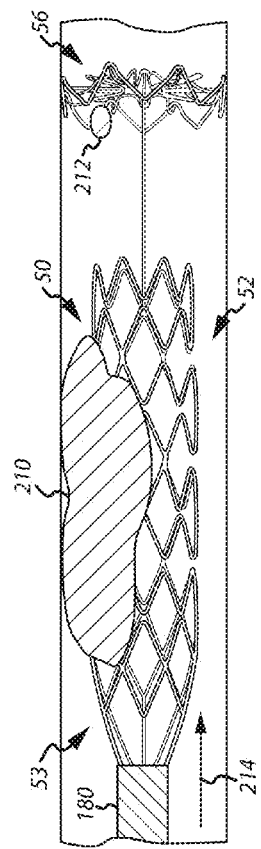

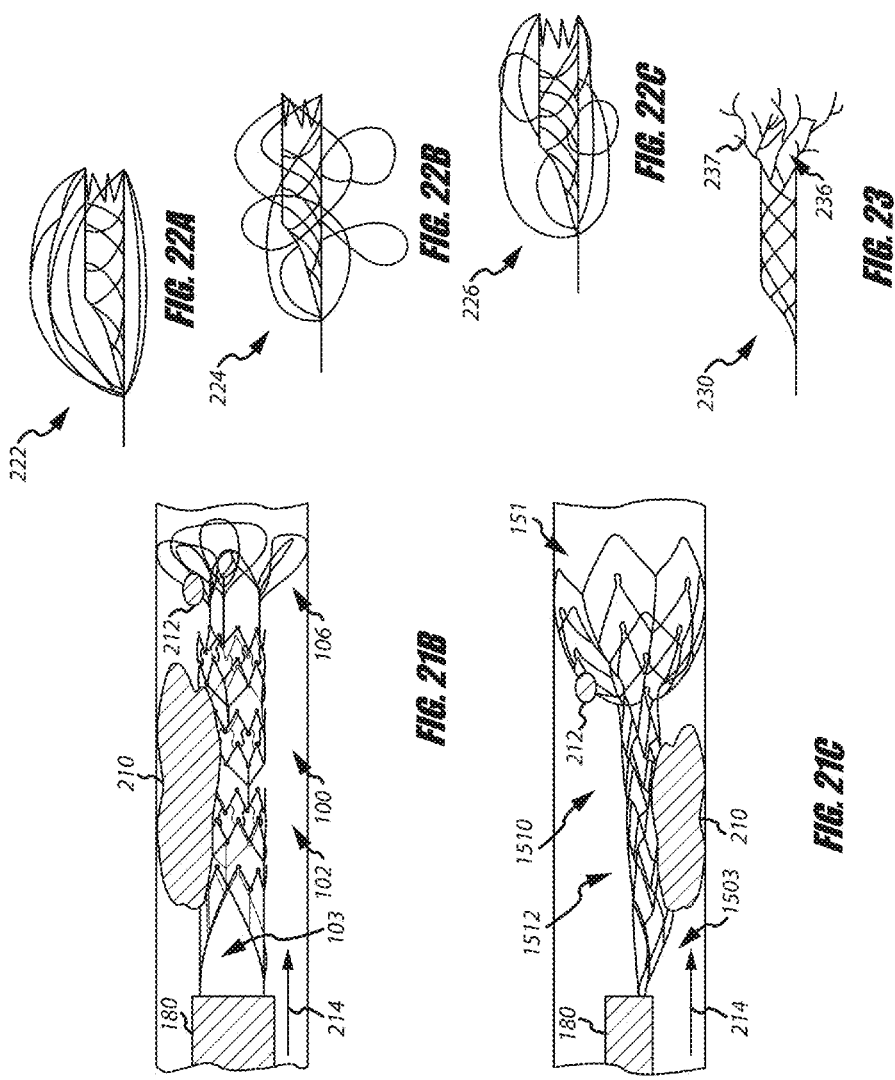

VASCULAR REMODELING DEVICE

CROSS-REFERENCE TO RELATED APPLICATIONS

The present application claims priority to U.S. Provisional Patent App. No. 61/420,275, filed Dec. 6, 2010 and U.S. Provisional Patent App. No. 61/448,506, filed Mar. 2, 2011, which are hereby incorporated by reference in their entirety.

BACKGROUND

1. Field

The subject technology relates generally to vascular remodeling devices and to the manner of their positioning in vessels, and, more particularly, to remodeling devices having scaffolding distal sections and to the manner of their positioning at the junction of neurovascular bifurcations having an aneurysm and to remodeling devices having embolic protecting distal sections and to the manner of their use for clot retrieval.

2. Description of Related Art

Neurovascular or cerebral aneurysms affect about 5% of the population. Aneurysms may be located, for example, along arterial side walls (e.g., the aneurysm 10 illustrated in FIG. 1) and at arterial bifurcations (e.g., the aneurysm 20 illustrated in FIG. 2). The direction of fluid flow is generally indicated by the arrows 16, 26. The aneurysms 10, 20 each have a fundus 12, 22, a neck 14, 24, and a fundus-to-neck ratio or "neck ratio." If the neck ratio is greater than 2 to 1 or if the neck 14, 24 is less than 4 mm, the aneurysm 10, 20 may be treated with embolization coils alone because the coils will generally constrain themselves within the aneurysm 10, 20 without herniating into parent vessels. If the neck ratio is less than 2 to 1 or if the neck 14, 24 is greater than 4 mm, the aneurysms 10, 20 may be difficult to treat with embolization coils alone because the coils may be prone to herniating into parent vessels, as illustrated in FIG. 3A and FIG. 3B. Herniation of coils 18, 28 may cause arterial occlusion, stroke, and/or death. Compared to the bifurcation illustrated in FIG. 2, the efferent vessels of the bifurcation may be at substantially different angles, have substantially different sizes, and/or be a different quantity (e.g., three or more). Compared to the bifurcation illustrated in FIG. 2, the aneurysm 20 of the bifurcation may be offset with respect to the junction (e.g., having a neck substantially open to one efferent vessel), tilted with respect to a plane created by the vessels (e.g., into or out of the page), etc. Moreover, vasculature may include more than two efferent vessels (e.g., three efferent vessels in a trifurcation). Each of these would still be accurately characterized as a "bifurcation" herein.

In order to inhibit such herniation, tubular neck remodeling devices, for example Neuroform®, available from Boston Scientific, and Enterprise™, available from Cordis Neurovascular, may be used to keep coils or other materials within the fundus of the aneurysm and out of the vessels. Tubular remodeling devices generally consist of a braided wire or cut metallic stent or stents covering the neck of the aneurysm so that materials introduced into the fundus of the aneurysm do not herniate out of the aneurysm. As illustrated in FIG. 4A, tubular remodeling devices 40 are generally useful for side wall aneurysms 10. As illustrated in FIG. 4B and FIG. 4C, tubular remodeling devices 42, 44 are generally less useful for aneurysms 20 at bifurcations (e.g., the basilar tip area), for example because positioning/shaping the remodeling devices to preserve blood flow through the afferent and efferent vessels while also inhibiting herniation of coils 28 out of the aneurysm 20 can be difficult.

SUMMARY

In some embodiments described herein, an intraluminal vascular remodeling device or stent includes a tubular proximal portion and a distal portion. The proximal portion has an open cell design, a closed cell design, or a hybrid cell design having no reverse free-peaks for retrievability, good flexibility, and/or good wall apposition, or may be braided from a plurality of filaments. The proximal portion may include one or more tapered portions that allow the device to be retrievable. The distal portion includes a flower portion or a plurality of ring assemblies each including rings of different sizes and flexibilities. The proximal portion is connected to the distal portion by an intermediate portion that may include a plurality of straight or elongation struts or a unit cell of the proximal portion. The intermediate portion and the distal portion may be shaped into an umbrella shape or a reverse umbrella shape. The delivery device for the stent includes an outer sheath (e.g., a microcatheter) containing the stent in the compressed delivery state and a plunger configured to push the stent out of the outer sheath and to release the stent mechanically, chemically, or electrolytically. The plunger may also include a guidewire lumen for aid in positioning of the delivery device at the treatment area or for maintaining access distally after delivery of the device.

During deployment, the distal portion expands from the compressed delivery state, possibly to an expanded state, to a further expanded state that is substantially planar compared to the dimensions of the proximal portion. In some embodiments, the distal section is changed to a further expanded state in a "blooming" action, wherein the distal end of the distal section moves outwardly and proximally, and the proximal end of the distal section moves inwardly and distally. In some embodiments, the distal section is changed to a further expanded state in a "blooming" action, wherein the proximal end of the distal section moves outwardly and distally, and the distal end of the distal section moves inwardly and proximally.

The proximal portion is positioned in an afferent vessel and the distal portion is positioned in a bifurcation junction across the neck of an aneurysm. In some embodiments, at least a portion of certain struts or rings of the distal portion may contact the fundus of the aneurysm and/or be placed inside the aneurysm. The intermediate portion does not interfere with blood flow to efferent vessels. Before or after the stent is in position, embolic material is used to treat the aneurysm using the stent delivery catheter or a different catheter. The distal portion is configured to act as a scaffolding to prevent herniation of objects out of the neck and/or fundus of the bifurcation aneurysm. The distal portion may be configured to allow insertion of embolic material therethrough. The device may also or alternatively be used to treat or inhibit ischemic stroke or other diseases by retrieving thrombi or blood clots. The device may also treat stroke by providing revascularization before or during thrombus retrieval. The proximal section can trap a clot and the distal section can provide distal embolic protection by catching stray clots and clot fragments.

According to some embodiments, an intraluminal device of the present discloses comprises a proximal section configured to anchor in an afferent vessel; an intermediate section comprising a plurality of struts configured to allow perfusion to efferent vessels; and a distal section configured to act as a scaffolding to inhibit herniation of objects out of a neck of a bifurcation aneurysm; wherein each of the plurality of struts is coupled at a coupling to the distal section at a region between a proximal end of the distal section and a distal end of the distal section; wherein the distal section is biased to transition from a first configuration forming a substantially cylindrical shape to a second configuration forming a substantially planar shape when released from a catheter.

According to some embodiments, the proximal section may comprise a hybrid cell design comprising open cells and closed cells. The proximal section may comprise a plurality of repeating unit cells. The distal section may comprise at least one said unit cell and at least partially forms a semi-sphere, umbrella, reverse umbrella, or flower shape in an expanded state.

According to some embodiments, the proximal section may comprise a plurality of woven filaments. The proximal section may comprise at least one tapered portion. The proximal section may have a length between about 5 mm and about 30 mm. The proximal section may have a length between about 10 mm and about 20 mm. The intermediate section may have a length between about 0 mm and about 6 mm.

According to some embodiments, the substantially cylindrical shape may have an inner surface and an outer surface, and each of the inner surface and the outer surface of the substantially cylindrical shape may define a respective opposing proximal and distal side of the substantially planar shape in the second configuration. The distal section may have a smallest inner cross-sectional dimension in the second configuration that is less than a smallest inner cross-sectional dimension of the proximal section.

According to some embodiments, while transitioning from the first configuration to the second configuration, (i) a distal portion of the distal section may be configured to move radially outwardly and proximally relative to the coupling and (ii) a proximal portion of the distal section may be configured to move radially inwardly and distally relative to the coupling. While transitioning from the first configuration to the second configuration, the distal portion may move to an axial location substantially aligned with or proximal to the coupling. While transitioning from the first configuration to the second configuration, the distal portion may move radially outwardly to define, in the second configuration, an outermost cross-sectional dimension that is greater than an outermost cross-sectional dimension of the proximal section. While transitioning from the first configuration to the second configuration, the proximal portion may move to an axial location substantially aligned with or distal to the coupling. While transitioning from the first configuration to the second configuration, the proximal portion may move radially inwardly to define, in the second configuration, an innermost cross-sectional dimension that is less than an innermost cross-sectional dimension of the proximal section.

According to some embodiments, when transitioned from the first configuration to the second configuration, the proximal portion of the distal section may define a first lumen sized smaller than a second lumen defined by the proximal section.

According to some embodiments, the distal section may pivot about the coupling when transitioning from the first configuration to the second configuration.

According to some embodiments, while transitioning from the first configuration to the second configuration, (i) a distal portion of the distal section may be configured to move radially inwardly and proximally relative to the coupling and (ii) a proximal portion of the distal section may be configured to move radially outwardly and distally relative to the coupling. While transitioning from the first configuration to the second configuration, the proximal portion may move radially outwardly to define, in the second configuration, an outermost cross-sectional dimension that is greater than an outermost cross-sectional dimension of the proximal section. While transitioning from the first configuration to the second configuration, the distal portion may move radially inwardly to define, in the second configuration, an innermost cross-sectional dimension that is less than an innermost cross-sectional dimension of the proximal section.

According to some embodiments, the distal section may comprise a plurality of woven filaments. The proximal section and the distal section are integrally cut from a tube or a sheet. The proximal section and the distal section are comprised of the same material. The distal section may comprise a covering.

According to some embodiments, an intraluminal device of the present discloses includes a proximal section configured to anchor in an afferent vessel; an intermediate section configured to allow perfusion to efferent vessels; and a distal section comprising a first plurality of rings and a second plurality of rings; wherein the distal section is configured to act as a scaffolding to inhibit herniation of objects out of a neck of a bifurcation aneurysm; wherein the distal section is biased to transition from a first configuration to a second configuration when released from a sheath; wherein, while in the first configuration, the first plurality of rings and the second plurality of rings extend parallel to a longitudinal axis of the intraluminal device; and wherein, while in the second configuration, the first plurality of rings extend radially inwardly and the second plurality of rings extend radially outwardly.

According to some embodiments, the first plurality of rings may be more flexible than the second plurality of rings. Each of the first plurality of rings may have a largest dimension smaller than a diameter of the proximal portion and each of the second plurality of rings may have a largest dimension larger than a diameter of the proximal portion. The first and second plurality of ring assemblies each may comprise between about 1 and about 30 rings.

According to some embodiments, a method of manufacturing an intraluminal device, comprises: coupling a proximal section to a distal section by an intermediate section, the proximal section configured to anchor in an afferent vessel, the intermediate section configured to allow perfusion to efferent vessels, and the distal section configured to act as a scaffolding to inhibit herniation of objects out of a neck of a bifurcation aneurysm.

According to some embodiments, the method of manufacturing may further comprise cutting the proximal section from a sheet or a tube. Cutting the proximal section may comprise cutting a hybrid cell design. According to some embodiments, the method of manufacturing may further comprise cutting the distal section from a sheet or a tube. Cutting the distal section may comprise cutting a flower portion. Cutting the distal section may comprise cutting a plurality of rings. According to some embodiments, the method of manufacturing may further comprise cutting the intermediate section from a sheet or a tube.

According to some embodiments, coupling the proximal section to the distal section by the intermediate section may comprise integrally forming the proximal section, the distal section, and the intermediate section.

According to some embodiments, the method of manufacturing may further comprise weaving the proximal section from a plurality of filaments. According to some embodiments, the method of manufacturing may further comprise weaving the distal section from a plurality of filaments.

According to some embodiments, coupling the proximal section to the distal section by the intermediate section may comprise welding the proximal section to the intermediate section. Coupling the proximal section to the distal section by the intermediate section may comprise welding the distal section to the intermediate section.

According to some embodiments, the method of manufacturing may further comprise heat setting the proximal section to have an expanded state. According to some embodiments, the method of manufacturing may further comprise heat setting the distal section to have a further expanded state.

According to some embodiments, a method of treating an aneurysm at a junction of a bifurcation having an afferent vessel and efferent vessels, the aneurysm having a neck and a fundus, comprises: advancing a catheter proximate to the junction of the bifurcation, the catheter at least partially containing a device in a compressed state, the device comprising: a proximal section configured to anchor in an afferent vessel; an intermediate section configured to allow perfusion to efferent vessels; and a distal section configured to act as a scaffolding to inhibit herniation of objects out of a neck of a bifurcation aneurysm; expanding the distal section from the compressed state to a radially expanded state at the junction of the bifurcation, wherein a distal end of the distal section may move radially outwardly and proximally relative to the proximal section, and a proximal end of the distal section may move radially inwardly and distally relative to the proximal section.

According to some embodiments, the method of treating may further comprise expanding the proximal section within an afferent vessel proximal to the bifurcation after expanding the distal section.

According to some embodiments, the method of treating may further comprise inserting embolic material into the aneurysm. Inserting the embolic material may comprise inserting the embolic material from the catheter. Inserting the embolic material may comprise inserting the material through a lumen defined by the expanded distal section. Inserting the embolic material is before expanding the distal section. Inserting the embolic material is after expanding the distal section. Inserting the embolic material is during expanding the distal section. Inserting the embolic material may comprise inserting embolic coils. Inserting the embolic material may comprise inserting embolic fluid.

According to some embodiments, the method of treating may further comprise retrieving the distal section at least partially back into the catheter, and redeploying the distal section.

According to some embodiments, expanding the distal section may comprise releasing the device from the catheter. Releasing the device from the catheter may comprise mechanical detachment. Releasing the device from the catheter may comprise electrolytic detachment. According to some embodiments, the aneurysm may comprise a basilar tip aneurysm.

According to some embodiments, the intermediate section may comprise a plurality of struts and each of the plurality of struts may comprise a distal portion coupled, at a coupling, to the distal section at a region between a proximal end of the distal section and a distal end of the distal section.

According to some embodiments, a method of retrieving a clot from a vessel comprises advancing a catheter in the vessel distal to the clot, the catheter at least partially containing a device in a compressed state, the device including a proximal section and a distal section; deploying the device from at least partially inside the catheter to outside the catheter, wherein, during deployment, the proximal section self-expands alongside the clot and engages the clot; and the distal section self-expands to a further expanded state and is configured to catch stray clots or stray clot fragments, wherein the distal section has a second diameter in the further expanded state, the second diameter larger than the first diameter, wherein the distal end of the distal section moves outwardly and proximally, and the proximal end of the distal section moves inwardly and distally; or the proximal end of the distal section moves outwardly and distally, and the distal end of the distal section moves inwardly and proximally; retrieving the device and the clot (e.g., at least partially back into the catheter or another retrieval device); and removing the catheter from the vessel.

According to some embodiments, the vessel may have an inner diameter and the second diameter is the same as the inner diameter of the vessel. The proximal section may comprise a tapered portion. The proximal section may comprise a plurality of tapered portions. The proximal section may comprise a longitudinal slit at least partially defining edges and the edges overlap to form a coiled configuration.

According to some embodiments, during deployment, the edges may spring open to engage the clot. During retrieval, the edges may clamp down on the clot. The proximal section may comprise a hybrid cell design. The distal section may comprise a flower portion. The distal section may comprise a plurality of rings. The distal section may comprise a semisphere, umbrella, or reverse umbrella shape.

According to some embodiments, an intraluminal device comprises: a plurality of forward peaks, wherein at least some of the forward peaks are forward free-peaks; a plurality of reverse peaks; and a strut connected proximate to a tip of each said reverse peak.

According to some embodiments, at least some of the struts may be substantially straight. At least some of the struts may be s-shaped or c-shaped. At least some of the struts may be connected to a tip of at least some of said reverse peaks. At least some of the struts may be connected offset from a tip of at least some of said reverse peaks. A group of forward peaks and reverse peaks may form a unit cell and the device may comprise a plurality of connected unit cells repeating longitudinally along the device.

The intraluminal device may further comprise a tapered portion. The intraluminal device may further comprise a plurality of tapered portions.

According to some embodiments, a method of treating an aneurysm at a junction of a bifurcation having an afferent vessel and efferent vessels comprises advancing a catheter proximate to the junction of the bifurcation, the catheter at least partially containing a device in a compressed state, the device comprising: a proximal section configured to anchor in an afferent vessel; an intermediate section comprising a plurality of struts configured to allow perfusion to efferent vessels; and a distal section configured to act as a scaffolding to inhibit herniation of objects out of a neck of a bifurcation aneurysm; wherein each of the plurality of struts comprises a distal portion coupled, at a joint, to the distal section at a region of the distal section between a proximal end of the distal section and a distal end of the distal section; expanding the distal section from the catheter at the junction of the bifurcation, wherein each of the proximal end and the distal end may pivot about the joint, such that the distal section at least partially everts.

For purposes of summarizing the subject technology and the advantages that may be achieved over the prior art, certain objects and advantages of the subject technology are described herein. Of course, it is to be understood that not necessarily all such objects or advantages need to be achieved in accordance with any particular embodiment. Thus, for example, those skilled in the art will recognize that the subject technology may be embodied or carried out in a manner that achieves or optimizes one advantage or group of advantages as taught or suggested herein without necessarily achieving other objects or advantages as may be taught or suggested herein.

All of these embodiments are intended to be within the scope of the subject technology herein disclosed. These and other embodiments will become readily apparent to those skilled in the art from the following detailed description having reference to the attached figures, the subject technology not being limited to any particular disclosed embodiment(s).

BRIEF DESCRIPTION OF THE DRAWINGS

These and other features, aspects, and advantages of the subject technology are described with reference to the drawings of certain embodiments, which are intended to illustrate certain embodiments and not to limit the subject technology.

FIG. 1 illustrates an example embodiment of a side wall aneurysm.

FIG. 2 illustrates an example embodiment of a bifurcation having an aneurysm.

FIG. 3A illustrates an example embodiment of a side wall aneurysm with herniating embolization coils.

FIG. 3B illustrates an example embodiment of a bifurcation having an aneurysm with herniating embolization coils.

FIG. 4A illustrates an example embodiment of a side wall aneurysm treated with embolization coils and a tubular remodeling device.

FIG. 4B and FIG. 4C illustrates example embodiments of a bifurcation having an aneurysm treated with embolization coils and tubular remodeling devices.

FIG. 5A is a side elevational view of an example embodiment of a vascular remodeling device.

FIGS. 5B, 5C, and 5D are front elevational views of example embodiments of distal sections of the vascular remodeling device of FIG. 5A.

FIG. 7A and FIG. 7B illustrate an example embodiment of a method for treating an aneurysm using the device of FIG. 5A.

FIGS. 8A, 8B, and 8C illustrate example embodiments of vascular remodeling device detachment mechanisms.

FIG. 9A illustrates an example embodiment of a cut patterns in a hypotube for forming the device of FIG. 5A.

FIG. 9B illustrates the cut pattern of FIG. 9A rotated 90°.

FIG. 10A illustrates a perspective view of another example embodiment of a vascular remodeling device.

FIG. 10B illustrates a front elevational view of the device of FIG. 10A.

FIG. 10C illustrates an example embodiment of a cut pattern in a sheet or a hypotube for forming the device of FIG. 10A.

FIG. 11 illustrates an example embodiment of a treated aneurysm using the device of FIG. 10A.

FIGS. 12A, 12B, 12C, 12D, 12E, 12F, 12G, 12H, 12I, and 12J illustrate example embodiments of proximal sections of vascular remodeling devices.

FIG. 13A and FIG. 13B illustrate example embodiments of intermediate sections of vascular remodeling devices.

FIGS. 18A, 18B, 18C, 18D, and 18E illustrate an example embodiment of a method for treating an aneurysm using a vascular remodeling device.

FIGS. 19A, 19B, 19C, 19D, and 19E illustrate another example embodiment of a method for treating an aneurysm using a vascular remodeling device.

FIGS. 20A, 20B, and 20C illustrate another example embodiment of a method for treating an aneurysm using a vascular remodeling device.

FIGS. 21A, 21B, and 21C illustrate example embodiments of a method for clot retrieval using a vascular remodeling device.

FIGS. 22A, 22B, and 22C illustrate example embodiments of proximal sections of a vascular remodeling device.

FIG. 23 illustrates another example embodiment of a vascular remodeling device.

DETAILED DESCRIPTION

Although some embodiments and examples are described below, those of skill in the art will appreciate that the subject technology extends beyond the specifically disclosed embodiments and/or uses and obvious modifications and equivalents thereof. Thus, it is intended that the scope of the subject technology disclosed herein should not be limited by any particular embodiments described below.

The use of numerical values in the various ranges specified in this application, unless expressly indicated otherwise, are stated as approximations as though the minimum and maximum values within the stated ranges were both preceded by the word "about." Slight variations above and below the stated ranges may be used to achieve substantially the same results as values within the ranges. The disclosure of ranges is intended as a continuous range including every value between the minimum and maximum values recited as well as any ranges that can be formed by such values. Accordingly, the skilled person will appreciate that many such ratios, ranges, and ranges of ratios can be unambiguously derived from the data and numbers presented herein and all represent various embodiments of the subject technology.

FIG. 5A illustrates an example embodiment of a vascular remodeling device 50 comprising a scaffolding distal section 56. It will be appreciated that the device 50 may be more compliant than the vasculature in which it is deployed such that it may be somewhat misshapen after being deployed, and that certain shapes described herein are when the device 50 is an expanded (e.g., further expanded) state with no restriction. The device 50 comprises a proximal section 52 (or "bottom section" or "main body" or "stem" or "tubular portion" or "anchoring section"), an intermediate section 54 (or "middle section" or "open portion" or "flow section"), and a distal section 56 (or "top section" or "distal portion" or "flower" or "flower portion" or "umbrella section" or "treatment section"). The device 50 can be delivered via a catheter (e.g., microcatheter, guide catheter, delivery catheter) into a bifurcation to support an aneurysm filling device with minimal interruption of blood flow in afferent and efferent vessels. In some embodiments, the device 50 may be retrieved and/or repositioned.

Figure 6A:
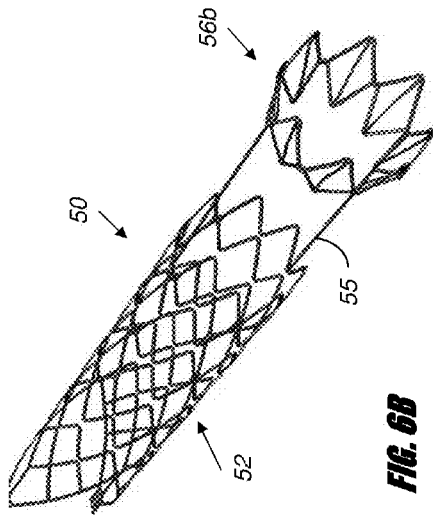
FIGS. 6A, 6B, 6C, and 6D illustrate an example embodiment of further expansion of the distal section of the vascular remodeling device of FIG. 5A.

The intermediate section 54 comprises a plurality of struts 55. The struts 55 may be straight, curved, or otherwise shaped, such as having design features like the proximal section 52 with the same or a different cell size. The struts 55 couple the proximal section 52 to the distal section 56. In some embodiments, each of the struts 55 contains at least two terminals ends. The terminal ends may connect to each of the proximal section 52 and the distal section 56. According to some embodiments, the distal section 56 contains a proximal portion (e.g., proximal end or proximal terminal end) and a distal portion (e.g., distal end or distal terminal end). A distal portion (e.g., distal end, or terminal distal end) of each of the struts 55 may couple to or join with the distal section 56 at a connection point, coupling location, or joint between the proximal end of the distal section 56 and the distal end of the distal section 56, as shown in FIG. 6A. The coupling location forms a joint about which at least some portions of distal section 56 may pivot. In some embodiments, at least some of the struts 55 connect with a distal portion thereof at a middle portion of the distal section 56. In some embodiments, at least some of the struts 55 connect with a distal portion thereof at the proximal end of the distal section 56. In some embodiments, at least some of the struts 55 connect with a distal portion thereof at the distal end of the distal section 56. In some embodiments, the struts 55 have a substantially rectangular or flat cross section (e.g., embodiments, in which the struts 55 comprise ribbons or uncut portions of a metallic tube or sheet). In some embodiments, the struts 55 have a substantially round (e.g., circular, elliptical, ovoid) cross section (e.g., embodiments, in which the struts 55 comprise round filaments). In some embodiments, the plurality of struts 55 comprises two struts 55. In some embodiments, the plurality of struts 55 comprises greater than two struts 55. In some embodiments, the plurality of struts 55 comprises between about two struts 55 and about twelve struts 55 (e.g., between about three struts 55 and about eight struts 55, three struts 55, four struts 55, five struts 55, six struts 55, seven struts 55, or eight struts 55). Other numbers of struts are also possible. In certain embodiments, the struts 55 may be equally spaced and/or oriented on opposite sides of the device 50 (e.g., two struts 180° apart along the circumference of the device 50, three struts 120° apart along the circumference of the device 50, four struts 90° apart along the circumference of the device 50, etc.). When the device 50 is placed at a bifurcation, the intermediate section 54 allows perfusion of blood to efferent vessels because the struts 55 do not block fluid flow.

In some embodiments, the proximal section 52 has a first diameter and the distal section 56 has a second diameter greater than the first diameter (e.g., due to the further expansion), which may cause the struts 55 to be angled or curved outwards from the longitudinal axis defined by the proximal section 52. In certain embodiments, the proximal section 52 has a round (e.g., circular, elliptical, or ovoid) cross section. In some embodiments, the proximal section 52 includes filaments having a substantially rectangular or flat cross section (e.g., embodiments, in which the proximal section 52 comprises ribbons or uncut portions of a metallic tube or sheet). In some embodiments, the proximal section 52 includes filaments having a substantially round (e.g., circular, elliptical, ovoid) cross section (e.g., embodiments, in which the proximal section 52 comprises round filaments). In some embodiments, the proximal section 52 comprises a plurality of z-shaped segments coupled by struts (e.g., as illustrated in FIG. 5A). Other patterns of the proximal section 52 are also possible, for example as described with respect to FIGS. 12A-12J. When the device 50 is placed at a bifurcation, the proximal section 52 provides anchoring of the device 50 in the afferent vessel. The proximal section 52 may also facilitate delivery, positioning, retrieval, and/or repositioning of the device 50.

In the example embodiment illustrated in FIG. 5A, the proximal end of the proximal section 52 comprises two tapered portions 53. The tapered portions 53 may allow the device 50 or portions thereof (e.g., the proximal section 52) to be retrieved back into a catheter. For example, if the device 50 is being pulled into a catheter, the tapered portions 53 may radially compress the proximal section 52. One tapered portion 53 or other numbers of tapered portion 53 are also possible.

FIGS. 5B-5D illustrate example embodiments of the distal section 56 in a further expanded state. The distal section 56 allows for safe and controlled placement of coils, and can be designed to support a certain packing density of coil. Upon deployment, the distal section 56 can be placed at the neck of an aneurysm and can cover the neck enough that aneurysm filling devices can still be positioned inside the aneurysm. In some embodiments, the distal section 56 comprises one or more of a mesh, a covering, additional filaments, etc. to achieve a fluid diversion effect, which may allow the omission of embolic material or an aneurysm filling device. FIG. 5C illustrates the distal section 56 of FIG. 5B with radiopaque markers (e.g., coils) around certain filaments. FIG. 5D illustrates the distal section 56 with fewer filaments than FIG. 5B.

In some embodiments, the device 50 comprises a self-expanding (e.g., super elastic, CoCr alloy, polyglycolic acid, polylactic acid, etc.) and/or a shape-memory material (e.g., Nitinol, shape memory polymers, etc.), thereby causing the device 50 to be self-expanding under certain conditions (e.g., not restrained by a catheter). In some embodiments, the proximal section 52, the intermediate section 54, and/or the distal section 56 may comprise different materials. For example, the distal section 56 may comprise polymer material while the proximal section 52 and the intermediate section 54 comprise metallic material, different polymer material, etc. For another example, the distal section 56 may comprise metallic material while the proximal section 52 and the intermediate section 54 comprise different metallic materials, polymer material, etc. Other combinations of materials are also possible. The device 50 can assume a low profile compressed state (e.g., confined within a catheter) for delivery. Upon deployment from the catheter, the device 50 expands (e.g., self-expands) from the compressed state to an expanded state. The distal section 56 expands (e.g., self-expands) to a further expanded state.

Figure 6B:
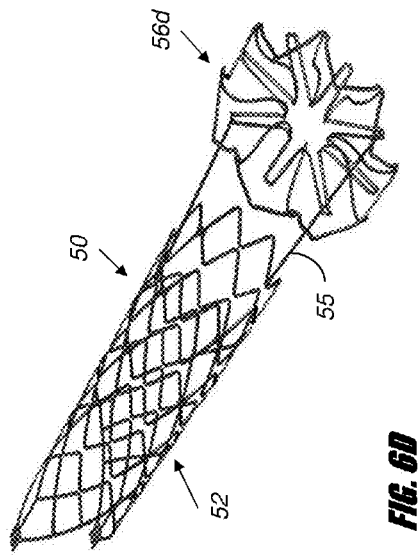
Figure 6C:
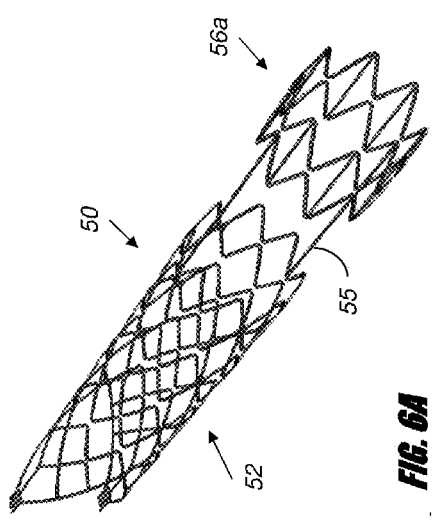
Figure 6D:
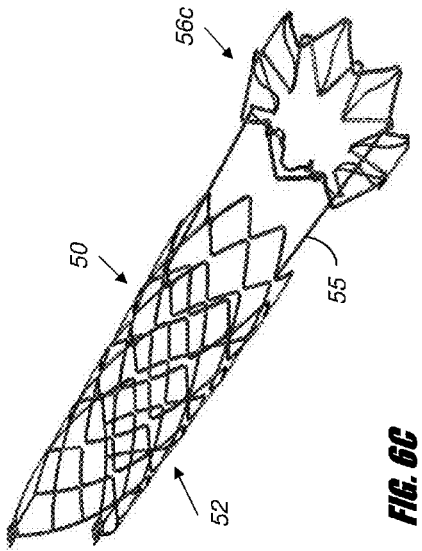

FIGS. 6A-6D illustrate an example embodiment of further expansion of the distal section 56 of the device 50. FIG. 6A illustrates the device 50 in the expanded state (e.g., having been released from a catheter). The distal section 56a in the expanded state has substantially the same diameter as the proximal section 52. FIG. 6B illustrates the distal section 56b in an intermediate further expanded state in which portions of the distal section 56b begin to assume a non-tubular shape, for example due to shape-setting of the distal section 56. FIG. 6C illustrates the distal section 56c in another intermediate further expanded state in which the portions of the distal section 56c further assume a non-tubular shape. FIG. 6D illustrates the distal section 56d in the further expanded state. FIG. 6D is a front perspective view of the device 50 of FIG. 5A. In the intermediate further expanded states and the further expanded state illustrated in FIG. 5A and FIGS. 6B-6D, the distal section 56, 56b, 56c, 56d has a larger diameter than the proximal section 52. As illustrated in FIG. 5A, in the further expanded state, the distal section 56 may be substantially flat (e.g., flat) or substantially planar (e.g., planar). In some embodiments, the distal section 56 changes or is biased to change to a further expanded state in a "blooming" action, wherein the distal portion of the distal section 56 moves radially outwardly and proximally relative to the coupling of the struts 55 to the distal section 56, and the proximal portion of the distal section 56 moves radially inwardly and distally relative to the coupling of the struts 55 to the distal section 56. In some embodiments, the distal section 56 is changed or is biased to change to a further expanded state in a "blooming" action, wherein the proximal end of the distal section 56 moves radially outwardly and distally relative to the coupling of the struts 55 to the distal section 56, and the distal portion of the distal section 56 moves radially inwardly and proximally relative to the coupling of the struts 55 to the distal section 56. It will be appreciated that such actions of distal section 56 or portions thereof may be performed relative to (a) the coupling of the struts 55 to the distal section 56, (b) the proximal section 52, (c) the struts 55, (d) the vessel, (e) the aneurysm, (f) a longitudinal axis of the device 50, or (g) any other object or location. It will be appreciated that the device 50 may not expand from the compressed state to the expanded state to the further expanded state, but that the proximal section 52 may expand from the compressed state to the expanded state while the distal section 56 may expand from the compressed state to the further expanded state (e.g., without the distal section 56 expanding from the compressed state to the expanded state). If the device 50 is deployed from a catheter, the distal section 56 may expand from the compressed state to the further expanded state, possibly via the expanded state, after being released from the catheter while the proximal section 52 still remains in the compressed state within the catheter.

According to some embodiments, as shown in FIGS. 6A-6D, the distal section 56 at least partially everts or is biased to evert at least partially during deployment. As used herein, "evert" and "eversion" refer to a process in which a structure turns inside-out. For example, a structure having a first surface initially facing inward and a second surface surface initially facing outward transitions during eversion such that at least one of the first surface ultimately faces outward and the second surface ultimately faces inward. Eversion may be complete or partial. Partial eversion refers to a process in which the structure begins, but does not necessarily complete, the transition described above. According to some embodiments, a length is defined between (i) each of the connection points at which the terminal ends of struts 55 are coupled to the distal section 56 and (ii) the proximal end of distal section 56. According to some embodiments, a length is defined between (i) each of the connection points at which the terminal ends of struts 55 are coupled to the distal section 56 and (ii) the distal end of distal section 56. According to some embodiments, each of the proximal end and the distal end may pivot about the connection points. According to some embodiments, each of the proximal end and the distal end may pivot about a section between the distal end and the proximal end, as shown in FIGS. 6A-6D.

According to some embodiments, the distal section 56 forms a substantially cylindrical (e.g., cylindrical) shape in a first, compressed state, as shown in FIG. 6A. The substantially cylindrical shape may define an inner surface facing radially inward and an outer surface facing radially outward. According to some embodiments, during or after deployment, the distal section 56 forms or is biased to form a substantially planar (e.g., planar) shape in a second, expanded state, as shown in FIG. 6D. The distal end and the proximal end of distal section 56 are substantially coplanar (e.g., coplanar) in the second, expanded state. For example, either one of the distal end and the proximal end may become concentric within the other. In the concentric configuration, the distal end and the proximal end may form inner and outer bands having different cross-sectional dimensions. According to some embodiments, after deployment, the inner surface and the outer surface of the substantially cylindrical shape define opposing sides of the substantially planar shape. For example, the inner surface of the substantially cylindrical shape may transition to a proximal side of the substantially planar shape, and the outer surface of the substantially cylindrical shape may transition to a distal side of the substantially planar shape. By further example, the inner surface of the substantially cylindrical shape may transition to a distal side of the substantially planar shape, and the outer surface of the substantially cylindrical shape may transition to a proximal side of the substantially planar shape.

In some embodiments, the device 50 comprises a radiopaque material such as platinum, platinum-iridium, and/or tantalum (e.g., being at least partially formed from the radiopaque material (e.g., having a radiopaque layer, consisting of a radiopaque material), including radiopaque markers). For example, the struts 55 may comprise radiopaque markers. For another example, certain segments of the distal section 56 may comprise radiopaque markers in the form of marker coils and/or marker bands (e.g., as illustrated in FIG. 5C). For yet another example, the struts 55 and certain segments of the distal section 56 may comprise radiopaque markers. For another example, structural struts in the distal section 56 can themselves comprise (e.g., be made from) a radiopaque material. For still another example, certain segments of the proximal section 52 (e.g., the tapered portions 53, tips of peaks) may comprise radiopaque markers. For another example, structural struts in the proximal section 52 can themselves comprise (e.g., be made from) a radiopaque material. It will be appreciated that the amount and type of radiopaque material used may depend, inter alia, on process technologies, desired level of radiopacity, mechanical properties of the radiopaque material, and corrosion properties of the radiopaque material.

In some embodiments, the device 50 is configured to be positioned at a junction of a bifurcation (e.g., a neurovascular bifurcation (e.g., the basilar tip area)) comprising at least one afferent vessel, efferent vessels, and an aneurysm having a fundus and a neck. For example, in some embodiments, the proximal section 52 is suitably dimensioned to fit in an afferent vessel of a bifurcation (e.g., having a diameter between about 2 mm and about 12 mm, having a diameter between about 6 mm and about 8 mm, having a diameter less than about 15 mm, having a diameter greater than about 1 mm). For example, in some embodiments, the proximal section 52 is suitably dimensioned to fit in an afferent vessel of a bifurcation. In certain embodiments, the device 50 is configured to act as a scaffolding to inhibit or prevent herniation or prolapse of objects (e.g., embolization coils, thrombi, etc.) out of a neck of an aneurysm. As used herein, "herniation" refers to relocation of coils from an implanted location (e.g., within an aneurysm) to a location other than the implanted location (e.g., outside an aneurysm). Herniation may or may not be caused by an external force acting on the coils. For another example, in some embodiments, the distal section 56 is dense enough that such objects cannot pass. In some embodiments, a relative amount of the distal section 56 or a portion thereof occupied by the filaments of the distal section 56 is between about 3% and about 25%. In some embodiments, a relative amount of the distal section 56 or a portion thereof occupied by the filaments of the distal section 56 is between about 3% and about 15%. In some embodiments, a relative amount of the distal section 56 or a portion thereof occupied by the filaments of the distal section 56 is at least about 5%. For another example, in some embodiments, the distal section 56 allows insertion of embolic material therethrough (e.g., through apertures or spaces between struts or filaments). In certain embodiments, the device 50 is configured to permit perfusion of fluid (e.g., blood) to efferent vessels of a bifurcation. For yet another example, in some embodiments, the intermediate section 54 is substantially devoid of a covering, mesh, or other material between the struts 55, thereby allowing fluid to flow substantially unimpeded.

FIG. 7A and FIG. 7B illustrate an example embodiment of a method for treating an aneurysm 20 using the device 50 at a confluence of afferent and efferent vessels or "junction" at a bifurcation 60 having an aneurysm 20. In some embodiments, the vessels are neurovascular or cranial. For example, the vasculature may include the basilar tip aneurysm, the middle cerebral artery, the anterior communicating artery, or the internal carotid bifurcation. In the case of a basilar tip aneurysm, which is at a junction in which the efferent vessels are at about a 90° angle to the afferent vessel, deployment of a conventional aneurysm-bridging stent between the efferent vessels and proximal to the aneurysm neck such that the device can hold embolic material in the aneurysm fundus may be difficult. Treatment of other vasculature, including other than neurovascular or cranial, is also possible.

FIG. 7A shows the proximal section 52 anchored in the afferent vessel and the distal section 56 placed across the neck of the aneurysm 20 after being deployed from a catheter (e.g., by being pushed out with a plunger, by retracting the catheter while the device remains stationary, etc.) and expanding as described herein. In some embodiments, the device 50 comprises a self-expanding and/or a shape-memory material that automatically expands (e.g., self-expands) towards an uncompressed state or does so upon the application of warm fluid (e.g., saline). The struts 55 of the intermediate section 54 allow fluid flow to the efferent vessels. FIG. 7B illustrates a plurality of embolization coils 62 inserted in the fundus of the aneurysm 20. It will be appreciated that the embolization coils 62 may be a single embolization coil or other embolic material (e.g., embolic fluid such as Onyx®, available from ev3). The embolization coils 62 or other embolic material may be inserted into the fundus before or after positioning of the device 50. In some embodiments, the embolization coils 62 are inserted in the fundus of the aneurysm 20 using the same catheter from which the device 50 is deployed. In some embodiments, the embolization coils 62 are inserted in the fundus of the aneurysm 20 using a different catheter than the catheter from which the device 50 is deployed. In certain such embodiments, a guidewire may be used to guide both catheters. The device 50 acts as a scaffolding to inhibit or prevent herniation or prolapse of objects such as the embolization coils 62 and/or thrombi out of the aneurysm 20. The distal section 56 of the device 50 may allow insertion of embolic material therethrough. The device 50 also allows perfusion of fluid (e.g., blood) from the afferent vessel(s) to the efferent vessel(s). If the position of the device 50 is not ideal, it can be pulled back inside the delivery catheters, repositioned, and redeployed at a different (e.g., better) position.

In some embodiments, final release of the device 50 is mechanical (e.g., by a release mechanism). In some embodiments, release of the device 50 is electrolytic (e.g., by applying a small current until a proximal tip of the tapered portions 53 corrodes away). In some embodiments, final release of the device 50 is chemical (e.g., by dissolving a connecting portion with a biocompatible solvent such as DMSO). The delivery systems and catheter may then be withdrawn from the bifurcation 60, thereby leaving or permanently positioning the device 50 at the junction of the bifurcation 60.

FIGS. 8A-8C illustrate example embodiments of release mechanisms that may be used to decouple the device 50 from a pusher wire or other portion of a delivery catheter. These and other release mechanisms may also be used for other devices described herein. In some embodiments, the release mechanism comprises a corrodible wire (e.g., for electrolytic detachment). In some embodiments, the release mechanism comprises a chemically reactive substance (e.g., dissolvable by DMSO). In some embodiments, the release mechanism comprises a mechanical release mechanism.

FIG. 8A illustrates a release mechanism 80 comprising a guidewire or catheter portion comprising an expanded end portion 81 (having a larger diameter than the portion proximal thereto) and a device proximal end portion comprising a plurality of fingers 82. When the device is confined within a catheter, the compression of the device material causes the fingers 82 to lock around the expanded end portion 81 and to couple the device proximal end portion to the guidewire or catheter portion. The device may optionally be released by causing the device proximal end to exit the catheter (e.g., by pushing a guidewire and/or pulling a catheter), at which point the fingers 82 may flex outwardly and lose grip on the expanded portion 81 (e.g., as illustrated in FIG. 8B). Alternatively, the device proximal end portion may comprise the expanded portion 81 and the guidewire or catheter portion may comprise the plurality of fingers 82.

FIG. 8C illustrates an example embodiment of an electrolytic release mechanism 85 comprising interlocking pieces 86, 87. A guidewire or a catheter portion comprises the piece 86 and the device proximal end portion comprises the piece 87, although a reverse configuration and other piece shapes are also possible. Unlike the expanded end portion 81 and the fingers 82 of the embodiment of FIG. 8A and FIG. 8B, the interlocking pieces 86, 87 are not configured to be released from each other. Although illustrated as proximal to the pieces 86, 87, a marker band 89 may surround the pieces 86, 87. The device may optionally be released by applying an electrical current and causing a narrow portion 88 of the device (e.g., proximal (e.g., immediately proximal) to the "bumper" or "glue dome") to dissolve, thereby releasing the distal end portion of the guidewire or the catheter portion and the device. In embodiments comprising a marker band 89, the marker band 89 may also be released from the guidewire or catheter portion and remain with the device by being distal to the narrow portion 88.

It will be appreciated that the term "permanently" does not mean that the device 50 is impossible to remove and/or reposition a later time. In some embodiments, the delivery catheter or a different catheter may be used to retrieve or reposition the device 50. In certain embodiments, the device 50 may be retracted into a catheter after being deployed. The device 50 may then be repositioned, for example, at a new rotational position, more proximal or distal to an afferent vessel and/or an efferent vessel, etc, or may be completely removed from the body, for example prior to delivery of a new device (e.g., a different device 50). Once the user is satisfied with the repositioned properties of the device 50 (e.g., size, position, rotation, shape, interaction with the vessels, etc.), the device 50 may be released.

FIG. 9A and FIG. 9B illustrate an example embodiment of a vascular remodeling device 50 at a stage of an example manufacturing process comprising cutting and shaping a metallic tube (e.g., a laser cut hypotube), FIG. 9B being rotated 90° with respect to FIG. 9A. Other tube diameters are also possible. A laser may cut out portions of the tube, leaving a plurality of filaments in the proximal section 52, struts 55 in the intermediate section 54, and a plurality of filaments in the distal section 56. Other cutting methods (e.g., chemical etch, mechanical cutting, etc.) are also possible.

FIG. 10A illustrates an example embodiment of a vascular remodeling device 100 comprising a scaffolding distal section 106. It will be appreciated that the device 100 may be more compliant than the vasculature in which it is deployed such that it may be somewhat misshapen after being deployed, and that certain shapes described herein are when the device 100 is an expanded (e.g., further expanded) state with no restriction. The device 100 comprises a proximal section 102 (or "bottom section" or "main body" or "stem" or "tubular portion" or "anchoring section"), an intermediate section 104 (or "middle section" or "open portion" or "flow section"), and a distal section 106 (or "top section" or "distal portion" or "flower" or "flower portion" or "umbrella section" or "treatment section"). The device 100 can be delivered via a catheter (e.g., microcatheter) into a bifurcation to support an aneurysm filling device with minimal interruption of blood flow in afferent and efferent vessels. In some embodiments, the device 100 may be retrieved and/or repositioned if needed.

The intermediate section 104 couples the proximal section 102 to the distal section 106. The intermediate section may comprise reduced material compared to the distal section 106 and/or the proximal section 102 to reduce interruption of fluid flow to efferent vessels and/or to reduce the risk of potential obstruction of efferent vessels. The intermediate section 104 comprises a plurality of struts 105. The struts 105 may be straight, curved, or otherwise shaped, such as having design features like the proximal section 102 with the same or a different cell size. The struts 105 couple the proximal section 102 to the distal section 106. In some embodiments, the struts 105 have a substantially rectangular or flat cross section (e.g., embodiments, in which the struts 105 comprise ribbons or uncut portions of a metallic tube or sheet). In some embodiments, the struts 105 have a substantially round (e.g., circular, elliptical, ovoid) cross section (e.g., embodiments, in which the struts 105 comprise round filaments). In some embodiments, the intermediate section 104 has a length between about 0 mm and about 6 mm. In embodiments in which the intermediate section 104 has a length of about 0 mm, the distal section 106 may be directly coupled to the proximal section 102, and the proximal section 102 may comprises a pattern and/or porosity that allows perfusion to efferent vessels.

In certain embodiments, the struts 105 are integrally fabricated with the proximal section 102 and the distal section 106, for example as described with respect to FIG. 10C. In embodiments in which all sections 102, 104, 106 of the device 100 are integrally fabricated by being cut from the same tube or sheet, the device 100 is of single-piece construction. In certain embodiments, the struts 105 are made from a different piece and are attached (e.g., welded, glued, adhered, mechanically crimped, mechanically swaged, braided, physical vapor deposited, chemical vapor deposited, etc.) to each of the proximal section 102 and the distal section 106. Separately formed struts 105 allows the struts 105 to be a different material from the proximal section 102 and the distal section 106, although it will be appreciated that flat pieces of metal may also comprise multiple sections comprising different metals. In some embodiments, the struts 105 comprise biocompatible metal and/or biocompatible polymer. In some embodiments, the struts 105 comprise radiopaque material (e.g., in the form of a radiopaque core, cladding, coating, small coiled wire, marker band, etc.), which can act as radiopaque markers for improved visibility of the device 100 during a procedure and/or following optional implantation.

In some embodiments, the plurality of struts 105 comprises two struts 105. In some embodiments, the plurality of struts 105 comprises greater than two struts 105. In some embodiments, the plurality of struts 105 comprises between about two struts 105 and about twelve struts 105 (e.g., between about three struts 105 and about eight struts 105, three struts 105, four struts 105, five struts 105, six struts 105, seven struts 105, or eight struts 105). Other numbers of struts 105 are also possible. In some embodiments, the struts 105 may be equally spaced and/or oriented on opposite sides of the device 100 (e.g., two struts 180° apart along the circumference of the device 100, three struts 120° apart along the circumference of the device 100, four struts 90° apart along the circumference of the device 100, etc.). In some embodiments, the number of struts 105 corresponds to the number of distal section ring assemblies described herein. When the device 100 is placed at a bifurcation, the intermediate section 104 allows perfusion of blood to efferent vessels because the struts 105 do not block fluid flow.

The proximal section 102 may be flexible and yet have enough radial force to anchor or maintain the position of the device 100 at a bifurcation after deployment (e.g., to inhibit or prevent longitudinal migration of the device 100). In certain embodiments, the proximal section 102 has a first diameter and the distal section 106 has a second diameter greater than the first diameter (e.g., due to expansion of the distal section ring assemblies), which may cause the struts 105 to be angled or curved outwards from the longitudinal axis defined by the proximal section 102. In certain embodiments, the proximal section 102 has a round (e.g., circular, elliptical, or ovoid) cross section. In some embodiments, the proximal section 102 includes filaments having a substantially rectangular or flat cross section (e.g., embodiments, in which the proximal section 102 comprises ribbons or uncut portions of a metallic tube or sheet). In some embodiments, the proximal section 102 includes filaments having a substantially round (e.g., circular, elliptical, ovoid) cross section (e.g., embodiments, in which the proximal section 102 comprises round filaments). In some embodiments, the proximal section 102 comprises a combination open cell and closed cell design and coupling struts (e.g., as illustrated in FIG. 10A), described in further detail herein. In certain such embodiments, the proximal section 102 may achieve good flexibility and/or have good vasculature conformance. In some embodiments, the proximal section 102 comprises a plurality of woven filaments.

When the device 100 is placed at a bifurcation, the proximal section 102 provides anchoring of the device 100 in the afferent vessel. The proximal section 102 may also facilitate delivery, positioning, retrieval, and/or repositioning of the device 100. In some embodiments, the proximal end of the proximal section 102 comprises a detachment portion, for example a detachment mechanism described herein, for example with respect to FIGS. 8A-8C.

In certain embodiments, the proximal section 102 is fully retrievable back into a catheter, which can allow repositioning of portions of the device 100. In certain embodiments, the proximal section 102 and the intermediate section 104 are fully retrievable back into a catheter, which can allow repositioning of portions of the device 100. In certain embodiments, the proximal section 102, the intermediate section 104, and the distal section 106 are fully retrievable back into a catheter, which can allow repositioning of portions (e.g., the entirety) of the device 100.

FIG. 10A illustrates an embodiment in which the proximal end of the proximal section 102 comprises two tapered portions 103. The tapered portions 103 may allow the device 100 or portions thereof (e.g., the proximal section 102) to be retrieved back into a catheter. For example, if the device 100 is being pulled into a catheter, the tapered portions 103 may radially compress the proximal section 102.

The distal section 106 may perform a variety of functions, for example providing support to embolic material such as embolic coils and/or diversion of blood flow away from an aneurysm. The distal section 106 may be atraumatic (e.g., comprising flexible materials, atraumatic shapes, etc.) to inhibit damaging or rupturing aneurysms. The distal section 106 may be self-aligning to accommodate possible misalignment between the afferent vessel and the neck of the aneurysm. The distal section 106 or portions thereof (e.g., certain rings or other features described herein) may be self-conforming to irregular contours of the neck of the aneurysm.

FIG. 10B illustrates an example embodiment of the distal section 106 in an expanded state. The distal section 106 allows for safe and controlled placement of coils, and can be designed to support a certain packing density of coil. Upon deployment, the distal section 106 can be placed at the neck (e.g., at least partially inside the fundus) of an aneurysm and can cover the neck to reduce the effective neck size enough that aneurysm filling devices can still be positioned inside the aneurysm. The distal section 106 comprises a plurality of ring assemblies. In some embodiments, each ring assembly comprises a first ring 107, a second ring 108, and a third ring 109. The first ring 107 has a first stiffness, the second ring 108 has a second stiffness, and the third ring 109 has a third stiffness. In certain embodiments, the first stiffness of the first ring 107 is greater than the second stiffness of the second ring 108 and the third stiffness of the third ring 109 (e.g., to provide good support to embolic material). In certain embodiments, the third stiffness of the third ring 109 is less than the first stiffness of the first ring 107 and the second stiffness the second ring 108 (e.g., to provide good conformability and to be less traumatic to the aneurysm).

In certain embodiments, the rings 107, 108, 109 are integrated with the proximal section 102 (e.g., being cut from the same tube or sheet). In embodiments in which all sections 102, 104, 106 of the device 100 are integrally fabricated by being cut from the same tube or sheet, the device 100 is of single-piece construction. Single-piece construction may allow for easier manufacturing. In certain embodiments, the rings 107, 108, 109 are formed separately from the proximal portion 102 and are attached (e.g., welded, glued, adhered, mechanically crimped, mechanically swaged, braided, physical vapor deposited, chemical vapor deposited, etc.). In certain such embodiments, the rings 107, 108, 109 may comprise different material than the proximal section 102. For example, the rings 107, 108, 109 may comprise platinum, platinum-iridium, or a polymer and the proximal section 102 may comprise Nitinol or CoCr alloy. Other combinations of materials are also possible. Separate or multiple-piece construction may allow for independent selection of materials that are suited for the intended use. In certain embodiments, some of the rings 107, 108, 109 are integrated with the proximal section 102 (e.g., being cut from the same tube or sheet) and others of the rings 107, 108, 109 are formed separately from the proximal portion and are attached (e.g., welded, glued, adhered, mechanically crimped, mechanically swaged, braided, physical vapor deposited, chemical vapor deposited, etc.). Combination construction may allow easier fabrication than purely multiple-piece construction and also some material selection advantages.

In some embodiments, the third ring 109 and/or the second ring 108 is/are configured to conform to the contours of the anatomy and/or to self-align to the anatomy in the case of misalignment between the distal end 106 of the device 100 and the aneurysm and/or in the case of offset (e.g., long length, short length) between the afferent vessel and the neck of the aneurysm. In certain embodiments, the second stiffness of the second ring 108 is less than the first stiffness of the first ring 107 and is greater than the third stiffness of the third ring 109. Stiffness of the rings 107, 108, 109 may be influenced, for example, by having different dimensions and/or by different heat treatment processes (e.g., resistive and/or inductive heat treatment processes). In some embodiments, a largest dimension of the ring 107 is smaller than a diameter of the proximal end 102 of the device 100 in an expanded state. In some embodiments, a largest dimension of the ring 109 is larger than a diameter of the proximal end 102 of the device 100 in an expanded state. In some embodiments, the distal section 102 comprises between about 1 and about 30 rings. In some embodiments, each ring assembly of the distal section 102 comprises between about 1 and about 30 rings. In some embodiments, the distal section 106 comprises one or more of a mesh, a covering, additional filaments, etc. to achieve a fluid diversion effect, which may allow the omission of embolic material or an aneurysm filling device.

FIG. 10C illustrates an example embodiment of a vascular remodeling device 100 at a stage of an example manufacturing process comprising cutting and shaping a metallic sheet. A laser or electrochemical etching may cut out portions of the sheet, leaving a plurality of unit cells in the proximal section 102, struts 105 in the intermediate section 104, and a plurality of rings in the distal section 106. In the embodiment illustrated in FIG. 10C, the proximal section 102, the intermediate section 104, and the distal section 106 are integrally formed from the metallic sheet and not cut away from each other. In some embodiments in which all sections 102, 104, 106 of the device 100 are integrally fabricated by being cut from the same tube or sheet, the device 100 is of single-piece construction. The cut may be defined by features such as a thickness t of the filaments, effective length $l_e$ of the proximal section 102, tapered length $l_t$ of the proximal section 102, and the number of unit cells in the proximal section 102. In some embodiments, the width w is between about 0.02 mm and about 0.2 mm. In some embodiments, the width w is between about 0.03 mm and about 0.1 mm. In some embodiments, the width w is about 0.05 mm. Other widths w are also possible. The width w of the filaments may be uniform throughout the device 100, or may vary depending on location. For example, struts connecting unit cells may be thicker than struts within unit cells. In some embodiments, the length of a unit cell is between about 1 mm and about 7 mm. In some embodiments, the length of a unit cell is between about 2 mm and about 5 mm. Other unit cell lengths are also possible. The dimensions described herein, including for example dimensions described with respect to FIG. 9A and FIG. 9B, may be uniform throughout the proximal section 102 of the device 100, or may vary depending on location (e.g., increasing from proximal to distal, decreasing from proximal to distal, combinations thereof, and the like). Dimensions may be selected, for example, to accommodate certain vasculature, for flexibility, for wall conformance, etc.

After cutting or chemical etching, the sheet may be reshaped (e.g., into a tube) and the device 100 may be heat treated to impart shape setting to at least the proximal section 102 and the distal section 106. The shape setting process may include several steps comprising, for example, successively shapes using appropriate tooling to stretch and confine the cut sheet into a new shape during the heat treatment. At the end of the each heat treatment step, the cut sheet assumes the shape in which it was confined during the heat treatment process. After shape setting the device 100, the distal section 106 may be reshaped and the device 100 may be further heat treated to impart further shape setting to at least the distal section 106. For example, the rings 107, 108, 109 may be shape set to take the shape illustrated in FIG. 10A and FIG. 10B. According to some embodiments, while in a first, compressed state, each of a first plurality of rings (e.g., one or more of rings 107, rings 108, and rings 109) and each of a second plurality of rings (e.g., one or more others of rings 107, rings 108, and rings 109) extends parallel to a longitudinal axis of the device 50, as shown in FIG. 10C. According to some embodiments, while in the second, expanded state, each of the first plurality of rings extends or is biased to extend radially inwardly and each of the second plurality of rings extends or is biased to extend radially outwardly, as shown in FIG. 10A and FIG. 10B. According to some embodiments, while in the second, expanded state, each of the first plurality of rings extends or is biased to extend radially outwardly, and each of the second plurality of rings extends or is biased to extend radially inwardly. According to some embodiments, the first plurality of rings may be any of rings 107, 108, 109. According to some embodiments, the second plurality of rings may be any of rings 107, 108, 109. As shown in FIG. 11, a bias, as described herein, may allow one or more rings to be disposed against an inner surface of an aneurysm 110.

The final shape (e.g., further expanded state) and size may obtained by several such steps. For the final shape, there may be a slit along the length of the device 100 (e.g., the opposite sides of the sheet are not joined), or the edge(s) can be welded or otherwise joined together by other methods to form a complete tubular profile. Devices described herein may also be formed using cut a metallic tube that is reshaped after being cut, although it will be appreciated that the properties of the initial tube and the pattern of the cut may be different.

In some embodiments, the device 100 comprises a self-expanding (e.g., super elastic, CoCr alloy, such as polyglycolic acid and polylactic acid, etc.) and/or a shape-memory material (e.g., comprising Nitinol, shape memory polymers, etc.), thereby causing the device 100 to be self-expanding under certain conditions (e.g., not restrained by a catheter). In some embodiments, the proximal section 102, the intermediate section 104, and/or the distal section 106 may comprise different materials (e.g., in addition to having different thicknesses as described herein). The device 100 can assume a low profile compressed state (e.g., confined within a catheter) for delivery. Upon deployment from the catheter, the device 100 expands (e.g., self-expands) from the compressed state to an expanded state. The distal section 106 expands (e.g., self-expands) to a further expanded state.

In some embodiments, the device 100 comprises a radiopaque material such as platinum, platinum-iridium, and/or tantalum (e.g., being at least partially formed from the radiopaque material (e.g., having a radiopaque layer, consisting of a radiopaque material), including radiopaque markers). For example, the struts 105 may comprise radiopaque markers. For another example, certain segments of the distal section 106 may comprise radiopaque markers and/or be made from radiopaque materials. For yet another example, the struts 105 and certain segments of the distal section 106 may comprise radiopaque markers. For still another example, certain segments of the proximal section 104 may comprise radiopaque markers. It will be appreciated that the amount and type of radiopaque material used may depend, inter alia, on price, desired level of radiopacity, mechanical properties of the radiopaque material, and corrosion properties of the radiopaque material.

In some embodiments, the device 100 is configured to be positioned at a junction of a bifurcation (e.g., a neurovascular bifurcation (e.g., the basilar tip area)) comprising at least one afferent vessel, efferent vessels, and an aneurysm having a fundus and a neck. For example, in some embodiments, the proximal section 102 is suitably dimensioned to fit in an afferent vessel of a bifurcation (e.g., having a diameter between about 2 mm and about 10 mm, having a diameter between about 1 mm and about 15 mm, having a diameter between about 6 mm and about 8 mm, having a diameter less than about 15 mm, having a diameter greater than about 1 mm). In some embodiments, the device 100 is configured to act as a scaffolding to inhibit or prevent herniation or prolapse of objects (e.g., embolization coils, thrombi, etc.) out of a neck of an aneurysm. For another example, in some embodiments, the distal section 106 is dense enough that such objects cannot pass. In some embodiments, a relative amount of the distal section 56 or a portion thereof occupied by the filaments of the distal section 56 is between about 3% and about 25%. In some embodiments, a relative amount of the distal section 56 or a portion thereof occupied by the filaments of the distal section 56 is between about 3% and about 15%. In some embodiments, a relative amount of the distal section 56 or a portion thereof occupied by the filaments of the distal section 56 is at least about 5%. For another example, in some embodiments, the distal section 106 allows insertion of embolic material therethrough (e.g., through apertures or spaces between struts or filaments). In some embodiments, the device 100 is configured to permit perfusion of fluid (e.g., blood) to efferent vessels of a bifurcation. For yet another example, in some embodiments, the intermediate section is substantially devoid of a covering, mesh, or other material between the struts 105, thereby allowing fluid to flow substantially unimpeded. Some embodiments of distal sections 106 comprising a plurality of ring assemblies may be easier to deploy than, for example distal sections comprising a flower portion (e.g., the distal section 56 of FIGS. 5A-5D).

FIG. 11 illustrates an example embodiment of a device 100 positioned at a junction of a basilar tip aneurysm 110. The proximal section 102 is anchored in the afferent or main vessel 112, the intermediate section 104 allows perfusion to the efferent vessels 114, and the distal section 116 acts as scaffolding to inhibit herniation of embolic material from the aneurysm 110. In some embodiments, positioning of the device 100 using the afferent vessel 112 as the delivery path for the device 100 may be accomplished as follows. The distal tip of a delivery catheter (e.g., microcatheter or other catheters that can be tracked through and reach the location of the aneurysm 110) is placed inside the aneurysm 110 or at the neck of the aneurysm 110. The device 100 is then is inserted in the proximal end of the catheter or may be positioned in the catheter prior to placement of the distal tip of the delivery catheter. The distal section 106 of the device 100 is then pushed out of the distal end of the catheter (e.g., using a push wire and pulling the catheter back), allowing the distal section 106 to expand (e.g., self-expand) either at least partially inside the aneurysm 110 (e.g., as illustrated in FIG. 11) or at the neck of the aneurysm 110 to conform to the contour of the neck of the aneurysm 110 and to span the neck of the aneurysm 110 or to reduce the effective size of the neck. The intermediate section 104 of the device 100 is then pushed out of the distal end of the catheter (e.g., using a push wire and pulling the catheter back), allowing the intermediate section 104 to expand (e.g., self-expand) in the junction of the bifurcation. The proximal section 102 of the device 100 is then pushed out of the distal end of the catheter (e.g., using a push wire and pulling the catheter back), allowing the proximal section 102 to expand (e.g., self-expand) in the afferent vessel 112 to maintain the position of the device 100. The device 100 can be fully retrieved inside the catheter, the position of the catheter can be adjusted, and the device 100 can be redeployed, for example to a more desirable position if the position of any section 102, 104, 106 after initial deployment of the device 100 was not as desired after initial deployment. Additionally or alternatively, the device 100 can be fully retrieved inside the catheter and a different catheter or the same catheter with a different device (e.g., a device 100 having different dimensions such as diameter of the proximal portion 102, length of the intermediate portion 104, etc.) can be deployed, for example at a more desirable position or with more desirable properties (e.g., better anchoring, better neck coverage, etc.). Once the device 100 is positioned, the device 100 can be detached from the catheter electrolytically, mechanically, or chemically. As described herein, for example with respect to FIGS. 18A-20C, embolic material may be placed in the aneurysm 110 before, after, and/or during positioning of the device 100. The catheter used to deliver the device 100 may be used to deliver embolic material into the fundus of the aneurysm 110. The distal section 106 may divert fluid flow from the aneurysm 110, which may allow the omission of embolic material or an aneurysm filling device. Other delivery methods of the device 100 and other devices described herein are also possible, and it will be appreciated that the basilar tip aneurysm was used merely as an example of a bifurcation.

Figure 12G:
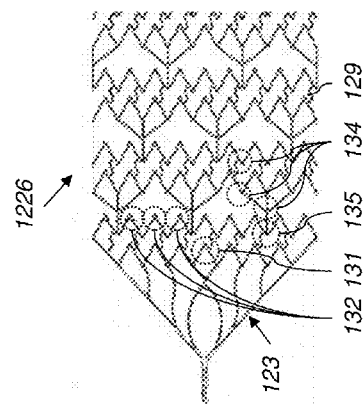
Figure 12F:
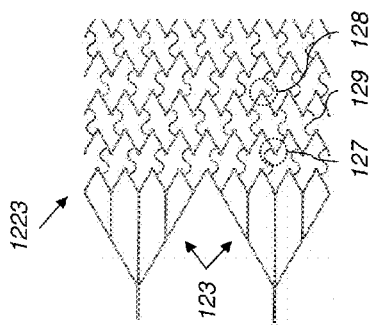
Figure 12B:
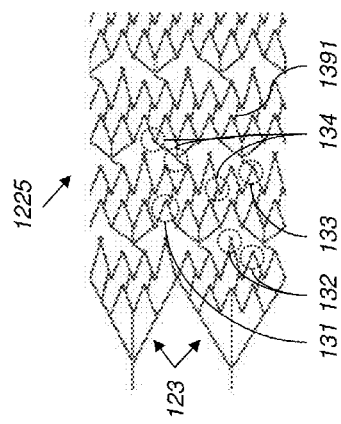
Figure 12E:
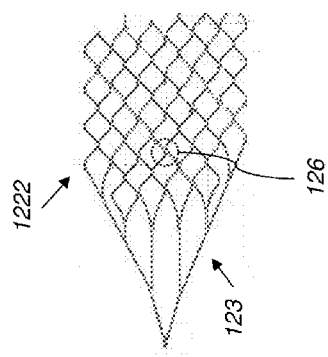
Figure 12A:
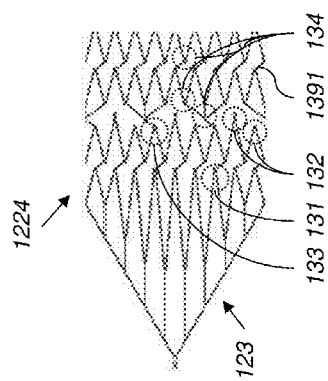

FIGS. 12A-12J illustrate example embodiments of proximal sections 1221, 1222, 1223, 1224, 1225, 1226, 1227, 1228, 1229, 1230 that may be incorporated into the devices described herein. FIG. 12A illustrates an example embodiment of a proximal section 1221 having an "open cell" design, identifiable by the reverse free-peaks 124 and the forward free-peaks 125. Open cell designs generally provide good flexibility and wall apposition, but may be difficult to retrieve, for example due to reverse free-peaks snagging or catching on the catheter during retrieval. FIG. 12B illustrates an example embodiment of a proximal section 1222 having a "closed cell" design, identifiable by the lack of any peaks due to contact of all cells at intersections 126. FIG. 12C illustrates another example embodiment of a proximal section 1223 having a "closed cell" design, identifiable by the lack of reverse free-peaks 127 and forward free-peaks 128, which are connected by struts 129. Closed cell designs are generally easy to deliver and to retrieve, but may be stiff and provide poor wall apposition (e.g., being prone to kinking rather than bending).

Figure 12D:
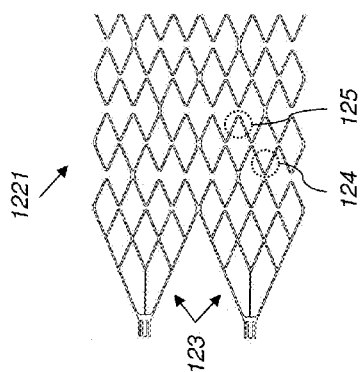

At least one aspect of the subject technology is the realization that a hybrid of open cell and closed cell designs can advantageously incorporate the advantages of each design and can avoid the potential drawbacks of each design. FIGS. 12D-12H illustrate example embodiments of proximal sections that are "hybrid" or "combination" designs including features of open cell designs and features of closed cell designs. FIG. 12D illustrates an example embodiment of a proximal section 1224 having a hybrid cell design. The proximal section 1224 comprises forward connected peaks 131, 133, forward free-peaks 132, and reverse connected peaks 134. The forward peaks 133 are connected to the next unit cell. The proximal section 1224 does not include any reverse free-peaks (124 of FIG. 12A). FIG. 12E illustrates an example embodiment of a proximal section 1225 having a hybrid cell design. The proximal section 1225 comprises forward connected peaks 131, 133, forward free-peaks 132, and reverse connected peaks 134. The forward peaks 133 are connected to the next unit cell. The proximal section 1225 does not include any reverse free-peaks (124 of FIG. 12A). FIG. 12F illustrates an example embodiment of a proximal section 1226 having a hybrid cell design. The proximal section 1226 comprises forward connected peaks 131, forward free-peaks 132, and reverse connected peaks 134. The proximal section 1226 further comprises valleys 135 connected to the next unit cell. The proximal section 1226 does not include any reverse free-peaks (124 of FIG. 12A). FIG. 12G illustrates an example embodiment of a proximal section 1227 having a hybrid cell design. The proximal section 1227 comprises forward connected peaks 131, forward free-peaks 132, and reverse connected peaks 134. The proximal section 1227 further comprises valleys 135 connected to the next unit cell. The proximal section 1227 does not include any reverse free-peaks (124 of FIG. 12A).

Figure 12H:
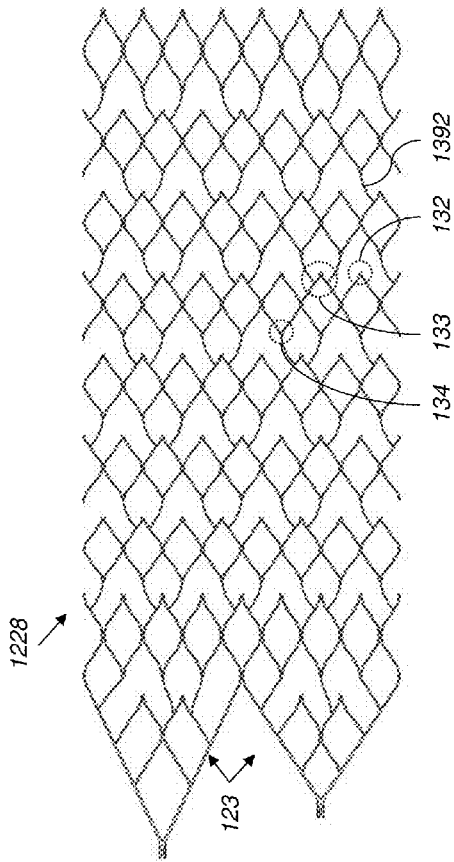
Figure 12G:
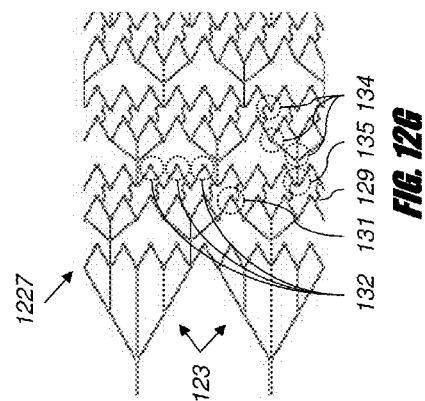
Figure 12I:
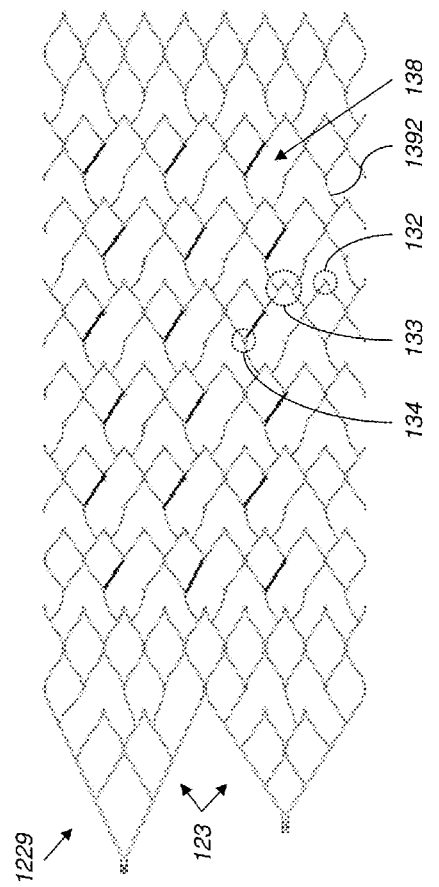

FIG. 12H illustrates an example embodiment of a proximal section 1228 having a hybrid cell design. The proximal section 1228 comprises forward connected peaks 133, forward free-peaks 132, and reverse connected peaks 134. The forward peaks 133 are connected to the next unit cell. Each unit cell comprises forward connected peaks 133 alternating with forward free-peaks 132. The proximal section 1228 further comprises peaks connected to the next unit cell. The proximal section 1228 does not include any reverse free-peaks (124 of FIG. 12A). FIG. 12I illustrates an example embodiment of a proximal section 1229 having a hybrid cell design. The proximal section 1229 comprises forward connected peaks 133, forward free-peaks 132, and reverse connected peaks 134. The forward peaks 133 are connected to the next unit cell. Each unit cell comprises forward connected peaks 133 alternating with forward free-peaks 132. The proximal section 1229 further comprises peaks connected to the next unit cell. The proximal section 1229 does not include any reverse free-peaks (124 of FIG. 12A). In contrast to the proximal section 1228 of FIG. 12H, the proximal section 1229 of FIG. 12I has fewer diagonal struts (e.g., missing in the area 138), which may provide better flexibility and/or wall apposition. FIG. 12J illustrates an example embodiment of a proximal section 1230 having a hybrid cell design. The proximal section 1230 comprises forward connected peaks 133, forward free-peaks 132, and reverse connected peaks 134. The forward peaks 133 are connected to the next unit cell. Each unit cell comprises forward connected peaks 133 alternating with forward free-peaks 132. The proximal section 1230 further comprises peaks connected to the next unit cell. The proximal section 1230 does not include any reverse free-peaks (124 of FIG. 12A). In contrast to the proximal section 1229 of FIG. 12I, the proximal section 1230 of FIG. 12J has straight struts 1391, which may be less prone to twisting during compaction. Combinations of the features of the cell patterns illustrated in FIGS. 12A-12I may be selected based on desired properties of the proximal section.

FIG. 12B, FIG. 12D, and FIG. 12F illustrate proximal sections 1222, 1224, 1226, respectively, having one tapered section 123, while FIG. 12A, FIG. 12C, FIG. 12E, FIG. 12G, FIG. 12H, FIG. 12I, and FIG. 12J illustrate proximal portions 1221, 1223, 1225, 1227, 1228, 1229, 1230, respectively, having two tapered sections 123. A single tapered section 123 may advantageously have only one detachment zone and be easy to release, while a plurality of tapered sections 123 may comprise a detachment zone proximal to each tapered section 123 and may be more difficult to release. A plurality of tapered sections 123 may have a shorter taper length $l_t$ and a longer effective length $l_e$ (FIG. 9A, FIG. 9B, and FIG. 10C), while a single tapered section 123 may have a longer taper length $l_t$ and a shorter effective length $l_e$ (FIG. 9A, FIG. 9B, and FIG. 10C) and may provide less anchoring in the afferent vessel. A plurality of tapered sections 123 may be more symmetrical and provide more uniform wall apposition. A plurality of tapered sections 123 may have less of a tension effect on the vessel, which may result from a single long tapered area applying force to a single side of the vessel. The effective length $l_e$ of the proximal section may be based on the intended anatomy. Longer lengths may be appropriate for more vessel wall apposition, while shorter lengths may be appropriate for traversing more tortuous anatomy. In some embodiments, the effective length $l_e$ of the proximal section is between about 5 mm and about 40 mm. In some embodiments, the effective length $l_e$ of the proximal section is between about 10 mm and about 30 mm. In some embodiments, the effective length $l_e$ of the proximal section is between about 10 mm and about 20 mm. Other effective lengths $l_e$ are also possible.

FIG. 12C, FIG. 12F, and FIG. 12G illustrate proximal sections 1223, 1226, 1227, respectively, comprising s-shaped struts 129 connecting certain forward peaks and reverse peaks. FIG. 12D, FIG. 12E, and FIG. 12J illustrate proximal portions 1224, 1225, 1230, respectively, comprising straight struts 1391 connecting certain forward peaks and reverse peaks. FIG. 12H and FIG. 12I illustrate proximal portions 1228, 1229 comprising c-shaped struts 1392 connecting certain forward peaks and reverse peaks. Connection struts having an s-shape or c-shape may be more flexible, but may be prone to twisting during compaction, while straight struts may be easier to compress but less flexible, which may be acceptable for hybrid cell designs already having suitable flexibility.

FIG. 12D and FIG. 12E illustrate proximal sections 1224, 1225 having tip-to-tip connections between forward and reverse peaks, which may provide a smaller compaction profile. FIG. 12F, FIG. 12G, FIG. 12H, and FIG. 12I illustrate proximal sections 1226, 1227, 1228, 1229 having at least partially offset tip-to-tip connections between forward and reverse peaks, which may provide increased flexibility and/or may increase vessel conformance.

FIG. 12D, FIG. 12E, FIG. 12H, FIG. 12I, and FIG. 12J illustrate proximal sections 1224, 1225, 1228, 1229, 1230, respectively, having tip-to-tip connections between forward and reverse peaks of unit cells, which may provide an easier compaction profile. FIG. 12F and FIG. 12G illustrate proximal sections 1226, 1227 having valley-to-tip connections between forward and reverse peaks of unit cells, which may provide good flexibility.

The patterns described herein can be repeated (e.g., repetition of rows of unit cells), adjusted (e.g., different angles, different lengths, different thicknesses, etc.), and/or combined (e.g., permutations of any of the features disclosed herein) based on the desired properties of the proximal section. In some embodiments, the proximal section may be flow diverting, which may allow the device to be used across sidewall aneurysms, for example as shown in FIG. 4A. In some embodiments, radiopaque markers are integrated into a portion (e.g., the distal peaks of the forward free-peaks, around the struts, etc.) of the proximal section that the user (e.g., physician) can use to monitor placement of the device.

FIG. 13A and FIG. 13B illustrate example embodiments of intermediate sections 1341, 1342 that may be incorporated into the devices described herein. FIG. 13A illustrates an example embodiment of an intermediate section 1341 comprising a plurality of straight struts 125. The number of struts 125 may be selected, for example, based on the expected weight of the embolic coils. For example, as coil weight increases, the number of struts 125 may increase. In some embodiments, the plurality of struts 125 comprises two struts 125. In some embodiments, the plurality of struts 125 comprises greater than two struts 125. In some embodiments, the plurality of struts 125 comprises three struts 125 (e.g., as illustrated in FIG. 13A). In some embodiments, the plurality of struts 125 comprises between about two struts 125 and about twelve struts 125 (e.g., between about three struts 125 and about eight struts 125, three struts 125, four struts 125, five struts 125, six struts 125, seven struts 125, or eight struts 125). Other numbers of struts 125 are also possible. In some embodiments, the struts 125 may be equally spaced and/or oriented on opposite sides of the device (e.g., two struts 180° apart along the circumference of the device, three struts 120° apart along the circumference of the device, four struts 90° apart along the circumference of the device, etc.).

FIG. 13B illustrates an example embodiment of an intermediate section 1342 comprising a straight strut 125 and two elongation struts 137 comprising openings. During compaction, the openings of the elongation struts 137 may collapse, thereby increasing the length of the elongation struts 137. In an example embodiment illustrated in FIG. 13B, upon compaction the straight strut 125 would maintain length, the middle elongation strut 137 would increase in length somewhat, and the top elongation strut 137 would increase in length the most. The portions of the distal section attached to the strut 125 and elongation struts would be differentiated, which may provide a good compaction profile. For example, referring again to FIG. 10C, the rings assemblies in the distal section 106 would be longitudinally spaced when compacted, and also may be less prone to tangling upon expansion.

Figure 14C:
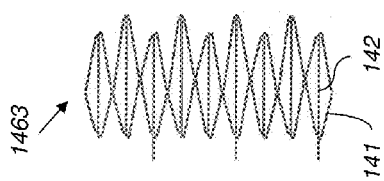
FIGS. 14A, 14B, 14C, 14D, 14E, and 14F illustrate example embodiments of distal sections of vascular remodeling devices.
Figure 14F:
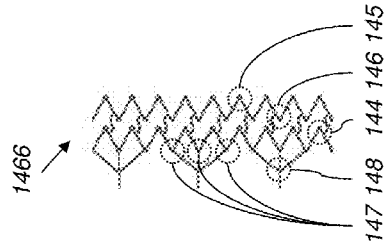
Figure 14B:
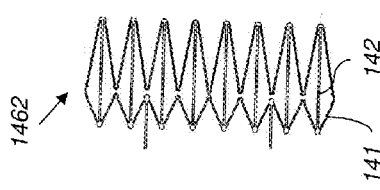
Figure 14E:
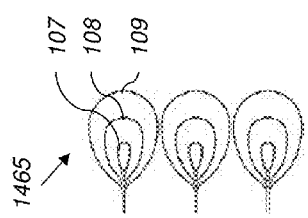
Figure 14A:
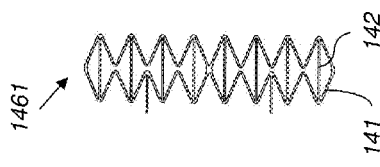
Figure 14D:
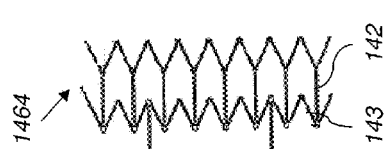

FIGS. 14A-14F illustrate example embodiments of distal sections that may be incorporated into the devices described herein. FIGS. 14A-14D illustrate example embodiments of distal sections 1461, 1462, 1463, 1464 that may be shaped to form a flower portion, for example as described herein with respect to FIGS. 5A-9B. FIG. 14A illustrates an example embodiment of a distal section 1461 comprising a plurality of open four-sided cells 141 including an internal strut 142. The internal struts 142 may provide increased surface area when the distal section 1461 acts as a scaffolding to inhibit herniation of objects out of the neck of an aneurysm and/or may help the distal section 1461 to form the further expanded or substantially planar configuration. FIG. 14B illustrates another example embodiment of a distal section 1462 comprising a plurality of open four-sided cells 141 including an internal strut 142. The internal struts 142 may provide increased surface area when the distal section 1462 acts as a scaffolding to inhibit herniation of objects out of the neck of an aneurysm and/or may help the distal section 1462 to form the further expanded or substantially planar configuration. The distal section 1462 includes asymmetric cells 141, which may expand to a greater diameter and cover aneurysms having wide necks or to reduce the effective neck size. FIG. 14C illustrates another example embodiment of a distal section 1463 comprising a plurality of open four-sided cells 141 including an internal strut 142. The internal struts 142 may provide increased surface area when the distal section 1463 acts as a scaffolding to inhibit herniation of objects out of the neck of an aneurysm and/or may help the distal section 1463 to form the further expanded or substantially planar configuration. The distal section 1463 includes disparate asymmetric cells 141, which may expand to a greater diameter and cover aneurysms having wide necks and/or which may provide a good compaction profile. The distal section 1463 includes cells 141 connected to the intermediate section (illustrated as three struts) at the tips of the cells 141, which may provide a good compaction profile. FIG. 14D illustrates another example embodiment of a distal section 1464 comprising a plurality of open six-sided cells 143 including an internal strut 142. The internal struts 142 may provide increased surface area when the distal section 1464 acts as a scaffolding to inhibit herniation of objects out of the neck of an aneurysm and/or may help the distal section 1464 to form the further expanded or substantially planar configuration. The distal section 1464 includes six-sided cells 143, which may expand to a greater diameter and cover aneurysms having wide necks and/or which may aid expansion into the further expanded configuration. The distal section 56 of FIG. 5A is an example embodiment of the distal section 1461 in an expanded or further expanded state. The distal sections 1462, 1463, 1464 may have a similar shape (e.g., substantially planar) in the expanded or further expanded state, for example with differences such as, for example, different diameters, peak sharpnesses, etc.

FIG. 14E illustrates an example embodiment of a distal section 1465 comprising a plurality of ring assemblies. As described with respect to FIGS. 10A-10C, the ring assemblies may each comprise a plurality of rings 107, 108, 109 having different flexibility, diameter, etc. In some embodiments, a distal section 1465 comprising a plurality of ring assemblies may be less prone to puncturing vasculature than the peaks of cells of flower portions. In some embodiments, a distal section 1465 comprising a plurality of ring assemblies may be easy to deploy, for example because the deployment force acts on different non-aligned angles. The distal section 106 of FIG. 10A is an example embodiment of the distal section 1465 in an expanded or further expanded state.

FIG. 14F illustrates an example embodiment of distal section 1466 comprising a unit cell of a proximal section having a hybrid cell design. The distal section 1466 comprises forward connected peaks 144, forward free-peaks 145, and reverse connected peaks 146, 147, 148. The distal section 1466 does not include any reverse free-peaks, which may enhance the ability of the distal section 1466 to be retrieved into a catheter. In some embodiments, the unit cell design of the distal section may be the same as the unit cell design of the proximal section. For example, the distal section 1466 may be combined with the proximal section 1226 of FIG. 12F or the proximal section 1227 of FIG. 12G. In some embodiments, the intermediate section may comprise long struts connecting the distal-most unit cell. In some embodiments, the intermediate section may comprise a unit cell.

Figure 15:
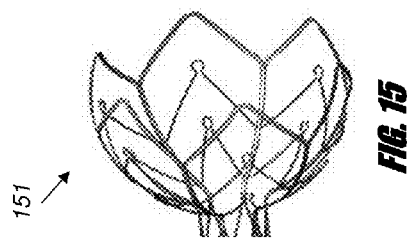
FIG. 15 illustrates an example embodiment of a distal section of a vascular remodeling device.

In some embodiments, the intermediate section and/or the distal section comprises an extension or another generation of the cell pattern of the proximal section that has been reshaped, for example into an approximate semi-sphere, umbrella, or reverse umbrella extending radially outward from the proximal section and then radially inward or outward towards the distal end. FIG. 15 illustrates an example embodiment of an intermediate section and distal section 151 comprising an extension of the cell pattern of the proximal section that has been reshaped into an approximate semi-sphere or umbrella shape. The device 151 may also be in a reverse-umbrella shape. In some embodiments, the section 151 may be easier to manufacture than other sections described herein. In some embodiments, the section 151 may be placed at a bifurcation of an aneurysm as described herein (e.g., at FIG. 7A and FIG. 7B). In some embodiments, the section 151 may be placed at least partially within a fundus of an aneurysm (e.g., at FIG. 11 and FIGS. 18A-20E). In certain such embodiments, the proximal section of the device may allow perfusion to efferent vessels.

In the embodiment illustrated in FIG. 15, the demarcation between the intermediate section and the distal section is not explicit. In some embodiments, the proximal half of the section 151 may be considered the intermediate section. In some embodiments, the portion of the section 151 that does not act as a scaffolding to inhibit herniation of objects out of the neck of an aneurysm may be considered the intermediate section. In some embodiments, the portion of the section 151 that allows perfusion to efferent vessels may be considered the intermediate section. In some embodiments, the intermediate section may at least partially overlap with the distal section. In some embodiments, the entire section after the proximal section may be considered the distal section (e.g., the length of the intermediate section is zero).

Any combination or permutation of the proximal, intermediate, and distal sections described herein, whether in FIGS. 12A-15 or elsewhere (e.g., the proximal section 222 of FIG. 22A, the proximal section 224 of FIG. 22B, the proximal section 226 of FIG. 22C, the distal section 236 of FIG. 23), may be used in an intraluminal device for aneurysm treatment, clot retrieval, or other uses. For example, referring again to FIG. 5A, the proximal section 52 is the proximal section 1221 of FIG. 12A, the intermediate section 54 is a plurality of struts 125 of FIG. 13A (two struts 55), and the distal section 56 is the distal section 1461 of FIG. 14A. For another example, referring again to FIG. 10C, the proximal section 102 is the proximal section 1225 of FIG. 12E, the intermediate section 104 is a plurality of struts 125 of FIG. 13A (three struts 105), and the distal section 106 is the distal section 1464 of FIG. 14D. It will be appreciated that a large number of permutations are possible by selecting a proximal section from amongst FIGS. 12A-12G (or equivalents or modifications thereof), selecting an intermediate section from amongst FIG. 13A and FIG. 13B (or equivalents or modifications thereof), selecting a distal section from amongst FIGS. 14A-14F (or equivalents or modifications thereof), and/or selecting an intermediate section and distal section from FIG. 15 (or equivalents or modifications thereof). Thus, the devices disclosed herein are not limited to any explicitly illustrated embodiment.

The proximal section, the intermediate section, and the distal section may be integrally formed from the metallic tube or sheet and not cut away from each other. In embodiments in which all sections of the device are integrally fabricated by being cut from the same tube or sheet, the device is of single-piece construction. Single-piece construction may allow for easier manufacturing. In some embodiments, some or all of the proximal section, the intermediate section, and the distal section may be formed separately, and the parts coupled together (e.g., by being welded, glued, adhered, mechanically crimped, mechanically swaged, braided, physical vapor deposited, chemical vapor deposited, etc.). For example, the proximal section and the distal section may be cut from a tube or a sheet and then coupled (e.g., welded, glued, adhered, mechanically crimped, mechanically swaged, braided, physical vapor deposited, chemical vapor deposited, etc.) by the struts (e.g., welded, glued, adhered, mechanically crimped, mechanically swaged, braided, physical vapor deposited, chemical vapor deposited, etc.). Certain portions of the proximal section, the intermediate section, and the distal section may be formed separately. For example, a proximal end segments may be cut from a tube or a sheet and then coupled (e.g., welded, glued, adhered, mechanically crimped, mechanically swaged, braided, physical vapor deposited, chemical vapor deposited, etc.) by connectors. In some embodiments, the distal section may comprise different material than the proximal section. For example, the distal section may comprise platinum, platinum-iridium, or a polymer and the proximal section may comprise Nitinol or CoCr alloy. Other combinations of materials are also possible. Separate or multiple-piece construction may allow for independent selection of materials that are suited for the intended use. In some embodiments, some parts of the distal section (e.g., peaks) are integrated with the proximal section (e.g., being cut from the same tube or sheet) and other parts of the distal section (e.g., struts between peaks) are formed separately from the proximal portion and are attached (e.g., welded, glued, adhered, mechanically crimped, mechanically swaged, braided, physical vapor deposited, chemical vapor deposited, etc.). Combination construction may allow easier fabrication than purely multiple-piece construction and also some material selection advantages.

Referring again to FIG. 9A and FIG. 9B, but also applicable to FIGS. 12A-15, the cut may be defined by features such as filament width w, lengths $l_1$ (e.g., length of a proximal end finger), $l_2$ (e.g., length of a proximal end segment including fingers), $l_3$ (e.g., length of a connector coupling proximal section unit cells, length between proximal section unit cells), $l_4$ (e.g., length of a proximal section unit cell, length of a proximal section unit cell portion), $l_5$ (e.g., length of intermediate section, length between proximal section and distal section), $l_6$ (e.g., length between distal section inward-facing peaks), $l_7$ (e.g., length of the distal section in a partially expanded state), heights $h_1$ (e.g., height of proximal end segment including fingers), $h_2$ (e.g., height of a proximal end finger in a first dimension), $h_3$ (e.g., height between proximal end fingers), $h_4$ (e.g., height of a proximal end finger in a second dimension), $h_5$ (e.g., height between free peaks), $h_6$ (e.g., height of distal section in the expanded state), and angles $a_1$ (e.g., angle of taper), $a_2$ (e.g., angle of reverse free peak, angle of reverse connected peaks), $a_3$ (e.g., angle of at least partially longitudinally projecting filaments), $a_4$ (e.g., angle of forward free peaks, angle of forward connected peaks), and $a_5$ (e.g., angle of distal end forward peaks). It will be appreciated that, for different patterns, the configuration and dimensions of certain features will also be different. For example, some cuts may not include certain of the dimensions described herein.

In some embodiments, the width w is between about 0.02 mm and about 0.2 mm. In some embodiments, the width w is between about 0.03 mm and about 0.1 mm. In some embodiments, the width w is about 0.05 mm. Other widths w are also possible. The width w of the filaments may be uniform throughout the device 100, or may vary depending on location. For example, struts connecting unit cells may be wider than struts within unit cells.

In some embodiments, the tapered length $l_t$ is between about 1.5 mm and about 20 mm. In some embodiments, the tapered length $l_t$ is between about 4 mm and about 15 mm. Other tapered lengths $l_t$ are also possible. In some embodiments, the effective length $l_e$ is between about 5 mm and about 40 mm. In some embodiments, the effective length $l_e$ is between about 10 mm and about 30 mm. In some embodiments, the effective length $l_e$ is between about 10 mm and about 20 mm. Other effective lengths $l_e$ are also possible.

In some embodiments, the length $l_2$ is between about 0.01 mm and about 2 mm. In some embodiments, the length $l_2$ is between about 0.05 mm and about 0.75 mm. Other lengths $l_2$ are also possible. In some embodiments, the length $l_3$ is between about 0.01 mm and about 3 mm. In some embodiments, the length $l_3$ is between about 0.1 mm and about 0.5 mm. Other lengths $l_3$ are also possible. In some embodiments, the length $l_4$ is between about 1 mm and about 7 mm. In some embodiments, the length $l_4$ is between about 2 mm and about 5 mm. Other lengths $l_4$ are also possible. In some embodiments, the length $l_5$ is between about 0 mm and about 8 mm. In some embodiments, the length $l_5$ is between about 0 mm and about 10 mm. In some embodiments, the length $l_5$ is between about 0 mm and about 6 mm. In some embodiments, the length $l_5$ is between about 6 mm and about 10 mm. In some embodiments, the length $l_5$ is about 8 mm. In some embodiments, the length $l_5$ is between about 0 mm and about 5 mm. Other lengths $l_5$ are also possible. In some embodiments, the length $l_6$ is between about 0.01 mm and about 3 mm. In some embodiments, the length $l_6$ is between about 0.05 mm and about 0.5 mm. Other lengths $l_6$ are also possible. In some embodiments, the length $l_7$ is between about 0.5 mm and about 10 mm. In some embodiments, the length $l_7$ is between about 1.5 mm and about 6 mm. Other lengths $l_7$ are also possible.

In some embodiments, the height $h_1$ is between about 0.01 mm and about 0.75 mm. In some embodiments, the height $h_1$ is between about 0.01 mm and about 0.5 mm. Other heights $h_1$ are also possible. In some embodiments, the height $h_4$ is between about 0.01 mm and about 0.25 mm. In some embodiments, the height $h_4$ is between about 0.01 mm and about 0.1 mm. Other heights $h_4$ are also possible. In some embodiments, the height $h_5$ is between about 0.25 mm and about 6 mm. In some embodiments, the height $h_5$ is between about 0.5 mm and about 3 mm. Other heights $h_5$ are also possible. In some embodiments, the height $h_6$ is between about 1.5 mm and about 6 mm in the expanded state. In some embodiments, the height of the distal section is between about 3 mm and about 15 mm in the further expanded state. Other heights $h_6$ and heights of the distal section in the further expanded state are also possible.

The dimensions described herein, including for example dimensions described with respect to FIG. 9A, may be uniform throughout the proximal section 102 of the device 100, or may vary depending on location (e.g., increasing from proximal to distal, decreasing from proximal to distal, combinations thereof, and the like). Dimensions may be selected, for example, to accommodate certain vasculature, for flexibility, for wall conformance, etc.

In some embodiments, other of the dimensions described herein may be uniform throughout the proximal section of the device, or may vary depending on location (e.g., increasing from proximal to distal, decreasing from proximal to distal, combinations thereof, and the like). Dimensions may be selected, for example, to accommodate certain microvasculature, for flexibility, for wall conformance, etc. In some embodiments, a reduced number of the connectors coupling proximal end segments may increase the flexibility of the proximal section of the device.

After cutting the tube or the sheet, the device may be reshaped and the device may be heat treated to impart shape setting to at least the distal section and/or the proximal section 122. The shape setting process may include several steps comprising, for example, successively shapes using appropriate tooling to stretch and confine the cut tube into a new shape during the heat treatment. At the end of the each heat treatment step, the cut tube or sheet assumes the shape in which it was confined during the heat treatment process. The final shape (e.g., further expanded state) and size may obtained by several such steps. In some embodiments in which a cut sheet is rolled to form a tube, there may be a slit along the length of the device (e.g., the opposite sides of the sheet are not joined), or the edge(s) can be welded or otherwise joined together by other methods to form a complete tubular profile. In certain such embodiments, the sides may be in contact or spaced.

Figure 16:
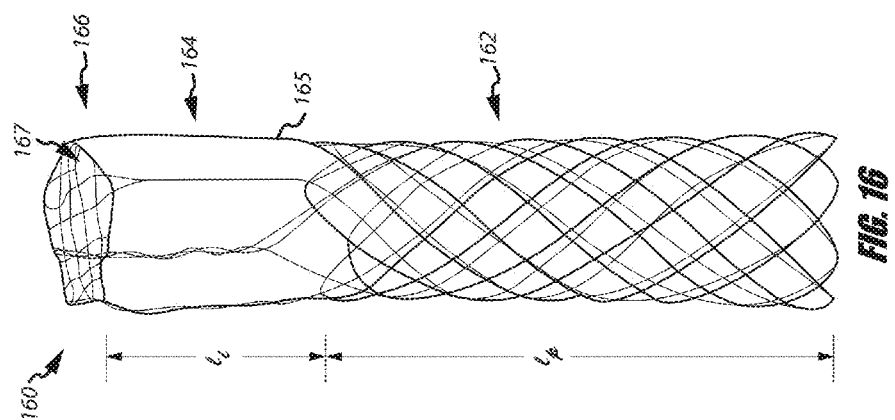
FIG. 16 illustrates a side-back perspective view of another example embodiment of a vascular remodeling device.

FIG. 16 illustrates an example embodiment of a vascular remodeling device 160 comprising a scaffolding distal section 166 that is woven from a plurality of filaments rather than being cut from a tube or a sheet. The device 160 comprises a proximal section 162, an intermediate section 164, and a distal section 166. The distal section 166 has a further expanded state, and the device 160 acts like an umbrella.

The intermediate section 164 comprises a plurality of struts 165. The struts 165 may be straight, curved, or otherwise shaped. In some embodiments, the struts 165 have a substantially rectangular or flat cross section (e.g., embodiments, in which the struts 165 comprise ribbons or uncut portions of a metallic tube or sheet). In some embodiments, the struts 165 have a substantially round (e.g., circular, elliptical, ovoid) cross section (e.g., embodiments, in which the struts 165 comprise round filaments). In the example embodiment illustrated in FIG. 16, the struts 165 comprise a plurality of wires twisted together. The struts 165 couple the proximal section 162 to the distal section 166. In some embodiments, the plurality of struts 165 comprises two struts 165. In some embodiments, the plurality of struts 165 comprises greater than two struts 165. In some embodiments, the plurality of struts 165 comprises between about two struts 165 and about twelve struts 165 (e.g., between about three struts 165 and about eight struts 165, three struts 165, four struts 165, five struts 165, six struts 165, seven struts 165, or eight struts 165). Other numbers of struts 165 are also possible. In certain embodiments, the struts 165 may be equally spaced and/or oriented on opposite sides of the device 160 (e.g., two struts 180° apart along the circumference of the device 160, three struts 120° apart along the circumference of the device 160, four struts 90° apart along the circumference of the device 160, etc.). When the device 160 is placed at a bifurcation, the intermediate section 164 allows flow to efferent vessels because the struts 165 do not block fluid flow. In some embodiments, the filaments in the intermediate section 164 have a width between about 0.02 mm and about 0.2 mm. In some embodiments, the filaments in the intermediate section 104 have a width between about 0.0035 mm and about 0.005 mm. In some embodiments, the filaments in the intermediate section 104 have a width between about 0.03 mm and about 0.1 mm. In some embodiments, the filaments in the intermediate section 104 have a width of about 0.05 mm. Other widths are also possible. It will be appreciated that in embodiments in which the struts 165 each comprise a plurality of filaments, the width of the struts may be approximately the width of the filaments multiplied by the number of filaments. The intermediate section 164 has a length $l_i$. In some embodiments, the length $l_i$ is between about 0 mm and about 6 mm. In some embodiments, the length $l_i$ is between about 0 mm and about 8 mm. In some embodiments, the length $l_i$ is between about 0 mm and about 10 mm. In some embodiments, the length $l_i$ is between about 6 mm and about 10 mm. In some embodiments, the length $l_i$ is about 8 mm. Other lengths $l_i$ are also possible.

In some embodiments, the proximal section 162 has a first diameter and the distal section 166 has a second diameter greater than the first diameter (e.g., due to the further expansion or weaving pattern), which may cause the struts 165 to be angled or curved outwards from the longitudinal axis defined by the proximal section 162. In some embodiments, the proximal section 162 has a round (e.g., circular, elliptical, or ovoid) cross section. In some embodiments, the proximal section 162 includes filaments having a substantially rectangular or flat cross section (e.g., embodiments in which the proximal section 162 comprises ribbons or uncut portions of a metallic tube or sheet). In some embodiments, the proximal section 162 includes filaments having a substantially round (e.g., circular, elliptical, ovoid) cross section (e.g., embodiments, in which the proximal section 162 comprises round filaments). In some embodiments, the proximal section 162 comprises a plurality of woven filaments (e.g., as illustrated in FIG. 16), which may provide good flexibility. When the device 160 is placed at a bifurcation, the proximal section 162 provides anchoring of the device 160 in the afferent vessel. The proximal section 162 may also facilitate delivery, positioning, and/or retrieval of the device 160. In some embodiments, the proximal section 162 has a foreshortening rate less than about 20%. In some embodiments in which the struts 165 comprise wire filaments, the proximal section 162 comprises the same wire filaments or the same type of wire filaments as the struts 165. In some embodiments, the filaments in the proximal section 162 have a width between about 0.02 mm and about 0.2 mm. In some embodiments, the filaments in the proximal section 162 have a width between about 0.0035 mm and about 0.005 mm. In some embodiments, the filaments in the proximal section 162 have a width between about 0.03 mm and about 0.1 mm. In some embodiments, the filaments in the proximal section 162 have a width of about 0.05 mm. Other widths are also possible. The proximal section 162 has a length $l_p$. In some embodiments, the length $l_p$ is between about 6.5 mm and about 60 mm. In some embodiments, the length $l_p$ is between about 14 mm and about 45 mm. In some embodiments, the length $l_p$ is between about 5 mm and about 40 mm. In some embodiments, the length $l_p$ is between about 10 mm and about 30 mm. In some embodiments, the length $l_p$ is between about 10 mm and about 20 mm. In some embodiments, the length $l_p$ is between about 10 mm and about 14 mm (e.g., about 12 mm). Other lengths $l_p$ are also possible.

The distal section 166 may have an umbrella shape. The distal section 166 allows for safe and controlled placement of coils, and can be designed to support a certain packing density of coil. Upon deployment, the distal section 166 can be placed at the neck of an aneurysm and can cover the neck enough that aneurysm filling devices can still be positioned inside the aneurysm. In some embodiments, the filaments in the distal section 166 have a width between about 0.02 mm and about 0.2 mm. In some embodiments, the filaments in the distal section 166 have a width between about 0.0015 mm and about 0.002 mm. In some embodiments, the filaments in the distal section 166 have a width between about 0.03 mm and about 0.1 mm. In some embodiments, the filaments in the distal section 166 have a width of about 0.05 mm. Other widths are also possible. In some embodiments, thinner filaments can be more atraumatic than large filaments. The distal section 166 has a diameter $d_d$. In some embodiments, the diameter $d_d$ is between about 1.5 mm and about 7 mm. In some embodiments, the diameter $d_d$ is between about 1.5 mm and about 6 mm. In some embodiments, the diameter $d_d$ is between about 3 mm and about 15 mm. Other diameters $d_d$ are also possible.

The distal section 166 comprises a plurality of perforations or cells 167 between the filaments. In some embodiments, the cells have a size of about 1 mm×about 1.2 mm. Other cell sizes and relative dimensions (e.g., equal length sides) are also possible. Other cell shapes (e.g., quadrilateral, parallelogram, rhombus, rectangle, square, hexagon, etc.) are also possible. In certain embodiments, a percentage of the distal section 166 covered by the filaments is between about 25% and about 40%. In certain embodiments, a percentage of the distal section 166 covered by the cells 167 is between about 60% and about 75%. Other porosities of the distal section 166 are also possible. In some embodiments, the distal section 166 may comprise a cover (e.g., a polymer cover). In certain embodiments, a porosity between about 60% and about 75% or lower or a cover may help to divert fluid flow away from an aneurysm, as well as providing more scaffolding support for embolic material in the aneurysm. In some embodiments, the distal section 166 comprises one or more of a mesh, a covering, additional filaments, etc. As described herein, for example with respect to FIG. 9A and FIG. 9B, heat treatment may be used to shape set the distal section 166 in the umbrella shape and the distal section 166 can have a further expanded shape.

In some embodiments, the device 160 comprises a self-expanding (e.g., CoCr alloy, such as polyglycolic acid and polylactic acid, etc.) and/or a shape-memory material (e.g., comprising Nitinol, shape memory polymers, etc.), thereby causing the device 160 to be self-expanding under certain conditions (e.g., not restrained by a catheter, temperature modified, etc.). In some embodiments, the proximal section 162, the intermediate section 164, and/or the distal section 166 may comprise different materials (e.g., in addition to having different thicknesses as described herein). The device 160 can assume a low profile compressed state (e.g., confined within a catheter) for delivery. Upon deployment from the catheter, the device 160 expands (e.g., self-expands) from the compressed state to an expanded state. The distal section 166 expands (e.g., self-expands) to a further expanded state.

In some embodiments, the device 160 comprises a radiopaque material such as platinum, platinum-iridium, and/or tantalum (e.g., being at least partially formed from the radiopaque material (e.g., having a radiopaque layer, consisting of a radiopaque material), including radiopaque markers). For example, the struts 165 may comprise radiopaque markers. For another example, certain segments of the distal section 166 may comprise radiopaque markers. For yet another example, the struts 165 and certain segments of the distal section 166 may comprise radiopaque markers. For still another example, certain segments of the proximal section 164 may comprise radiopaque markers. It will be appreciated that the amount and type of radiopaque material used may depend, inter alia, on price, desired level of radiopacity, mechanical properties of the radiopaque material, and corrosion properties of the radiopaque material.

In some embodiments, the device 160 is configured to be positioned at a junction of a bifurcation (e.g., a neurovascular bifurcation (e.g., the basilar tip area)) comprising at least one afferent vessel, efferent vessels, and an aneurysm having a fundus and a neck. For example, in some embodiments, the proximal section 162 is suitably dimensioned to fit in an afferent vessel of a bifurcation (e.g., having a diameter between about 3 mm and about 15 mm, having a diameter between about 1.5 mm and about 8 mm, having a diameter between about 1.5 mm and about 7 mm, having a diameter between about 1.5 mm and about 6 mm, having a diameter less than about 15 mm, having a diameter greater than about 1 mm). In some embodiments, the device 160 is configured to act as a scaffolding to inhibit or prevent herniation or prolapse of objects (e.g., embolization coils, thrombi, etc.) out of a neck of an aneurysm. For another example, in some embodiments, the distal section 166 is dense enough that such objects cannot pass. In some embodiments, a relative amount of the distal section 56 or a portion thereof occupied by the filaments of the distal section 56 is between about 3% and about 25%. In some embodiments, a relative amount of the distal section 56 or a portion thereof occupied by the filaments of the distal section 56 is between about 3% and about 15%. In some embodiments, a relative amount of the distal section 56 or a portion thereof occupied by the filaments of the distal section 56 is at least about 5%. For another example, in some embodiments, the distal section 166 allows insertion of embolic material therethrough (e.g., through the cells 167). In some embodiments, the device 160 is configured to permit perfusion of fluid (e.g., blood) to efferent vessels of a bifurcation. For yet another example, in some embodiments, the intermediate section is substantially devoid of a covering, mesh, or other material between the struts 165, thereby allowing fluid to flow substantially unimpeded.

Figure 17:
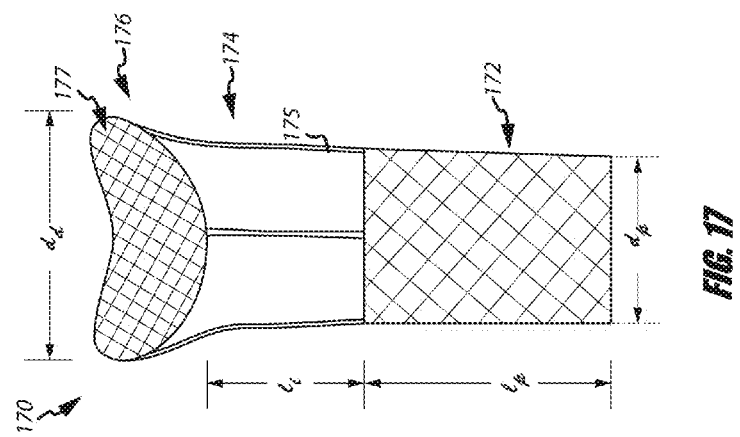
FIG. 17 illustrates a side elevational view of another example embodiment of a vascular remodeling device.

FIG. 17 illustrates an example embodiment of a vascular remodeling device 170 comprising a proximal section 172, an intermediate section 174 comprising a plurality of struts 175, and a distal section 176. As described herein, for example with respect to FIG. 16, the distal section 176 has a further expanded state, and the device 170 acts like an umbrella in that upon expansion the edges of the distal section 176 move longitudinally relative to the center of the distal section 176 and the edges of the distal section 176 move radially outward upon the longitudinal movement. In contrast to the device 160, the device 170 comprises a proximal section 172 and/or a distal section 176 comprising cells 177 cut from a sheet or a tube and then coupled to the intermediate section 174. The proximal section 172 has an effective length $l_p$ (e.g., a tapered portion is not shown, but may be proximal to the illustrated proximal section 172). In some embodiments, the length $l_p$ is between about 6.5 mm and about 60 mm. In some embodiments, the length $l_p$ is between about 14 mm and about 45 mm. In some embodiments, the length $l_p$ is between about 5 mm and about 40 mm. In some embodiments, the length $l_p$ is between about 10 mm and about 30 mm. In some embodiments, the length $l_p$ is between about 10 mm and about 20 mm. In some embodiments, the length $l_p$ is between about 10 mm and about 14 mm (e.g., about 12 mm). Other lengths $l_p$ are also possible. The intermediate section 174 has a length $l_i$. In some embodiments, the length $l_i$ is between about 0 mm and about 5 mm. In some embodiments, the length $l_i$ is between about 0 mm and about 6 mm. In some embodiments, the length $l_i$ is between about 0 mm and about 8 mm. In some embodiments, the length $l_i$ is between about 0 mm and about 10 mm. In some embodiments, the length $l_i$ is between about 6 mm and about 10 mm (e.g., about 8 mm). Other lengths $l_i$ are also possible.

The distal section 176 has an expanded or further expanded diameter $d_d$ that is greater than the expanded diameter $d_p$ of the proximal section 172. In some embodiments, the diameter $d_d$ is between about 1.5 mm and about 6 mm. Other diameters $d_d$ are also possible. In some embodiments, the diameter $d_p$ is between about 3 mm and about 15 mm. Other diameters $d_p$ are also possible.

FIGS. 18A-18E illustrate an example embodiment of a method for treating an aneurysm 20 using a vascular remodeling device (e.g., the devices 50, 100, 160, 170 described herein) at a confluence of afferent and efferent vessels or "junction" at a bifurcation having an aneurysm 20. In some embodiments, the vessels are neurovascular or cranial. FIG. 18A shows a catheter 180 (e.g., microcatheter) positioned in the afferent vessel and projecting into the bifurcation. FIG. 18B shows the distal section 186 being deployed at least partially within the fundus of the aneurysm 20 (e.g., by being pushed out with a plunger, by retracting the catheter while the device remains stationary, etc.) and expanding as described herein. In some embodiments, the distal section 186 abuts the neck of the aneurysm 20 but is not inserted in the aneurysm 20. In some embodiments, the device comprises a self-expanding and/or a shape-memory material that automatically expands (e.g., self-expands) towards an uncompressed state or does so upon the application of warm fluid (e.g., saline). As shown in FIG. 18C and FIG. 18D, a second catheter 181 is used to insert embolic coils 62 in the aneurysm 20 while the proximal section 182 of the device remains in the catheter 180. It will be appreciated that the embolization coils 62 may be a single embolization coil or other embolic material (e.g., embolic fluid such as Onyx®, available from ev3). The device acts as a scaffolding to inhibit or prevent herniation or prolapse of objects such as the embolization coils 62 and/or thrombi out of the aneurysm 20. The second catheter 181 is then removed, and the catheter 180 is removed to deploy the proximal section 182 in the afferent vessel. The device also allows perfusion of fluid (e.g., blood) from the afferent vessel(s) to the efferent vessel(s).

FIGS. 19A-19E illustrate another example embodiment of a method for treating an aneurysm 20 using a vascular remodeling device (e.g., the devices 50, 100, 160, 170 described herein) at a confluence of afferent and efferent vessels or "junction" at a bifurcation having an aneurysm 20. In some embodiments, the vessels are neurovascular or cranial. FIG. 19A shows a catheter 180 (e.g., microcatheter) positioned in the afferent vessel and projecting into the bifurcation. FIG. 19B shows the distal section 186 being deployed at least partially within the fundus of the aneurysm 20 (e.g., by being pushed out with a plunger, by retracting the catheter while the device remains stationary, etc.) and expanding as described herein. In some embodiments, the distal section 186 abuts the neck of the aneurysm 20 but is not inserted in the aneurysm 20. In some embodiments, the device comprises a self-expanding and/or a shape-memory material that automatically expands (e.g., self-expands) towards an uncompressed state or does so upon the application of warm fluid (e.g., saline). FIG. 19C shows the entire device including the proximal section 182 being released from the catheter 180 and the catheter 180 being removed prior to inserting a second catheter 181. The proximal section 182 anchors the device in the afferent vessel. As shown in FIG. 19C and FIG. 18D, a second catheter 181 is used to insert embolic coils 62 in the aneurysm 20. It will be appreciated that the embolization coils 62 may be a single embolization coil or other embolic material (e.g., embolic fluid such as Onyx®, available from ev3). The device acts as a scaffolding to inhibit or prevent herniation or prolapse of objects such as the embolization coils 62 and/or thrombi out of the aneurysm 20. The second catheter 181 is then removed. The device also allows perfusion of fluid (e.g., blood) from the afferent vessel(s) to the efferent vessel(s).

FIGS. 20A-20C illustrate yet another example embodiment of a method for treating an aneurysm 20 using a vascular remodeling device (e.g., the devices 50, 100, 160, 170 described herein) at a confluence of afferent and efferent vessels or "junction" at a bifurcation having an aneurysm 20. In some embodiments, the vessels are neurovascular or cranial. FIG. 20A shows a catheter 180 (e.g., microcatheter) positioned in the afferent vessel and projecting into the bifurcation. FIG. 20B shows the distal section 186 being deployed at least partially within the fundus of the aneurysm 20 (e.g., by being pushed out with a plunger, by retracting the catheter while the device remains stationary, etc.) and expanding as described herein. In some embodiments, the distal section 186 abuts the neck of the aneurysm 20 but is not inserted in the aneurysm 20. In some embodiments, the device comprises a self-expanding and/or a shape-memory material that automatically expands (e.g., self-expands) towards an uncompressed state or does so upon the application of warm fluid (e.g., saline). FIG. 20C shows the entire device including the proximal section 182 being released from the catheter 180 and the catheter 180 being removed prior. The proximal section 182 anchors the device in the afferent vessel. In contrast to the methods described with respect to FIGS. 18A-19E, a second catheter is not used to insert embolic material in the aneurysm 20. Rather, the embodiment of the device used in the method of FIGS. 20A-20C either comprises a porosity or covering that can divert fluid flow. The device also allows perfusion of fluid (e.g., blood) from the afferent vessel(s) to the efferent vessel(s).

Certain devices described herein may be advantageously used to treat aneurysms having a neck ratio (a ratio of fundus width to neck width) greater than about 2 to 1 and/or a neck width greater than about 4 mm. In treatment of such aneurysms, embolization coils may be prone to herniating into parent vessels because the size and/or shape of the aneurysm is not conducive to maintaining the coils in their inserted locus. In some embodiments, embolization coils are inserted in the fundus of the aneurysm after positioning a generally spherical device so that the embolization coils do not have an opportunity to herniate. It will be appreciated that certain devices described herein may also be used to treat aneurysms having a neck ratio less than about 2 to 1 and/or a neck width less than about 4 mm. In some embodiments, embolization coils are inserted in the fundus of the aneurysm before positioning a generally spherical device.

In some embodiments in which embolic material was previously inserted in an aneurysm but has herniated, certain devices described herein may be used as a "rescue device" to push the herniated material back into the aneurysm and to act as a scaffolding to inhibit or prevent further herniation or prolapse of the embolic material. In certain such embodiments, deployment of such devices may advantageously avoid traversal of the junction comprising the herniated material by wires or a catheter (e.g., there is no need to traverse wires or a catheter past the junction into an efferent vessel for positioning of the device as is generally needed to position tubular devices such as the devices 42, 44 illustrated in FIG. 4B and FIG. 4C), which may cause the herniated material to become tangled and/or dislodged and which may cause rupture of the aneurysm.

Certain devices described herein may also be useful to treat or inhibit ischemic stroke and other diseases by being used to retrieve thrombi or blood clots. U.S. patent application Ser. No. 12/918,795, filed on Feb. 20, 2009 and published as U.S. Patent Pub. No. 2011/0060212 on Mar. 10, 2011, describes methods of using devices having porous proximal sections for clot retrieval, and is hereby incorporated by reference in its entirety. The devices described herein comprise a distal section configured to act as a scaffolding to inhibit herniation of objects out of an aneurysm, and the distal section may also be used for distal protection during retrieval of soft or firm clots or clot fragments while allowing continued blood flow through the vessel due to the distal section not preventing fluid flow.

FIG. 21A illustrates an example embodiment of a method of capturing a clot 210 using a device 50 comprising a distal section 56 and a proximal section 52 within a catheter 180. The distal section 56 comprises a flower portion as described herein, for example with respect to FIGS. 5A-9B. In some embodiments, the distal end of the catheter 180 at least partially containing the device 50 in a compressed state is placed distal to the clot 210 as determined by the direction of blood flow indicated by the arrow 214. The catheter 180 is then retracted relative to the device 50. Upon exposure from the catheter 180, the device 50 expands (e.g., self-expands) from the compressed state to an expanded state. As described herein, the distal section 56 may expand (e.g., self-expand) to a further expanded state. In the further expanded state, the distal section 56 has a larger diameter than the proximal section 52. The proximal section 52 expands alongside the clot 210 and the distal section 56 expands distal to the clot 210. The flexibility of the proximal section 52 may be low to enhance resistance to clot 210 force (e.g., to cause the clot 210 to squish around the filaments). The clot 210 at least partially squeezes between the cells of the proximal section 52 and becomes lodged therein. In some embodiments, the distal section 56 expands to approximately the diameter of the vessel containing the clot. In this manner, the scaffolding of the distal section 56 can catch any clots or clot fragments that may be too small to be caught by the proximal section 52. The diameter and flexibility of the distal section 56 can provide good wall apposition to leave little (e.g., no) space for clot small clots or clot fragments (e.g., the clot fragment 212) to flow past while still allowing blood to flow through the vessel. Once the clot 210 and clot fragments are caught in the device 50, the device 50 is retrieved back into the catheter 180, for example by distally advancing the catheter 180 over the device 50 or pulling the device 50 into the catheter 180. In some embodiments, catheter 180 may be a guide catheter configured to receive the device 50 and clot 210 and/or clot fragments. During retrieval, the tapered portions 53 cause the device 50 to be radially compressed back into the catheter 180 along with the clot 210 and clot fragment 212. If pieces of the clot 210 break off during retrieval (e.g., the clot fragment 212), they can be caught in the distal section 56, which is the last portion of the device to be compressed into the catheter 180. The catheter 180 may then be removed from the body. The distal section 56 thus provides integrated embolic protection during the clot 210 retrieval procedure (e.g., nor requiring a separate filter or other embolic protection device). In some embodiments in which the device 50 is formed from a sheet, the edges of the sheet are not coupled in at least the proximal section 52 to leave a slot, and the edges may overlap to form a coiled configuration when viewed from the distal end to enhance interaction with the clot 210 (e.g., by springing open upon release from the catheter 180 and/or by acting as jaws that clamp down on the clot 210 during retrieval of the device 50). In some embodiments in which the device 50 is formed from a tube, the proximal section 52 comprises a longitudinal slot to form two edges, and the edges may overlap to form a coiled configuration when viewed from the distal end to enhance interaction with the clot 210 (e.g., by springing open upon release from the catheter 180 and/or by acting as jaws that clamp down on the clot 210 during retrieval of the device 50). In some embodiments in which the clot 210 is proximate to a bifurcation, the diameter of the distal section 56 may substantially span (e.g., span) the junction of a bifurcation, allowing perfusion to efferent vessels.

FIG. 21B illustrates an example embodiment of a method of capturing a clot 210 using a device 100 comprising a distal section 106 and a proximal section 102 within a catheter 180. The distal section 106 comprises a plurality of rings as described herein, for example with respect to FIGS. 10A-11. In some embodiments, the distal end of the catheter 180 at least partially containing the device 100 in a compressed state is placed distal to the clot 210 as determined by the direction of blood flow indicated by the arrow 214. The catheter 180 is then retracted relative to the device 100. Upon exposure from the catheter 180, the device 100 expands (e.g., self-expands) from the compressed state to an expanded state. As described herein, the distal section 106 may expand (e.g., self-expand) to a further expanded state. In the further expanded state, the distal section 106 has a larger diameter than the proximal section 102. The proximal section 102 expands alongside the clot 210 and the distal section 106 expands distal to the clot 210. The flexibility of the proximal section 102 may be low to enhance resistance to clot 210 force (e.g., to cause the clot 210 to squish around the filaments). The clot 210 at least partially squeezes between the cells of the proximal section 102 and becomes lodged therein. In some embodiments, the distal section 106 expands to approximately the diameter of the vessel containing the clot. In this manner, the scaffolding of the distal section 106 can catch any clots or clot fragments that may be too small to be caught by the proximal section 102. The diameter and flexibility of the distal section 106 can provide good wall apposition to leave little (e.g., no) space for clot small clots or clot fragments (e.g., the clot fragment 212) to flow past while still allowing blood to flow through the vessel. Once the clot 210 and clot fragments are caught in the device 100, the device 100 is retrieved back into the catheter 180, for example by distally advancing the catheter 180 over the device 100 or pulling the device 100 into the catheter 180. During retrieval, the tapered portions 103 cause the device 100 to be radially compressed back into the catheter 180 along with the clot 210 and clot fragment 212. If pieces of the clot 210 break off during retrieval (e.g., the clot fragment 212), they can be caught in the distal section 106, which is the last portion of the device to be compressed into the catheter 180. The catheter 180 may then be removed from the body. The distal section 106 thus provides integrated embolic protection during the clot 210 retrieval procedure (e.g., nor requiring a separate filter or other embolic protection device). In some embodiments in which the device 100 is formed from a sheet, the edges of the sheet are not coupled in at least the proximal section 102 to leave a slot, and the edges may overlap to form a coiled configuration when viewed from the distal end to enhance interaction with the clot 210 (e.g., by springing open upon release from the catheter 180 and/or by acting as jaws that clamp down on the clot 210 during retrieval of the device 100). In some embodiments in which the device 100 is formed from a tube, the proximal section 102 comprises a longitudinal slot to form two edges, and the edges may overlap to form a coiled configuration when viewed from the distal end to enhance interaction with the clot 210 (e.g., by springing open upon release from the catheter 180 and/or by acting as jaws that clamp down on the clot 210 during retrieval of the device 100). In some embodiments in which the clot 210 is proximate to a bifurcation, the diameter of the distal section 106 may substantially span (e.g., span) the junction of a bifurcation, allowing perfusion to efferent vessels.

FIG. 21C illustrates an example embodiment of a method of capturing a clot 210 using a device 1510 comprising a distal section 151 and a proximal section 1512 within a catheter 180. The distal section 151 comprises a semi-sphere or umbrella shape as described herein, for example with respect to FIG. 15. In some embodiments, the distal end of the catheter 180 at least partially containing the device 1510 in a compressed state is placed distal to the clot 210 as determined by the direction of blood flow indicated by the arrow 214. The catheter 180 is then retracted relative to the device 1510. Upon exposure from the catheter 180, the device 1510 expands (e.g., self-expands) from the compressed state to an expanded state. As described herein, the distal section 151 may expand (e.g., self-expand) to a further expanded state. In the further expanded state, the distal section 151 has a larger diameter than the proximal section 1512. The proximal section 1512 expands alongside the clot 210 and the distal section 151 expands distal to the clot 210. The flexibility of the proximal section 1512 may be low to enhance resistance to clot 210 force (e.g., to cause the clot 210 to squish around the filaments). The clot 210 at least partially squeezes between the cells of the proximal section 1512 and becomes lodged therein. In some embodiments, the distal section 151 expands to approximately the diameter of the vessel containing the clot. In this manner, the scaffolding of the distal section 151 can catch any clots or clot fragments that may be too small to be caught by the proximal section 1512. The diameter and flexibility of the distal section 151 can provide good wall apposition to leave little (e.g., no) space for clot small clots or clot fragments (e.g., the clot fragment 212) to flow past while still allowing blood to flow through the vessel. Once the clot 210 and clot fragments are caught in the device 1510, the device 1510 is retrieved back into the catheter 180, for example by distally advancing the catheter 180 over the device 1510 or pulling the device 1510 into the catheter 180. During retrieval, the tapered portions 1503 cause the device 1510 to be radially compressed back into the catheter 180 along with the clot 210 and clot fragment 212. If pieces of the clot 210 break off during retrieval (e.g., the clot fragment 212), they can be caught in the distal section 151, which is the last portion of the device to be compressed into the catheter 180. The catheter 180 may then be removed from the body. The distal section 151 thus provides integrated embolic protection during the clot 210 retrieval procedure (e.g., nor requiring a separate filter or other embolic protection device). In some embodiments in which the device 1510 is formed from a sheet, the edges of the sheet are not coupled in at least the proximal section 1512 to leave a slot, and the edges may overlap to form a coiled configuration when viewed from the distal end to enhance interaction with the clot 210 (e.g., by springing open upon release from the catheter 180 and/or by acting as jaws that clamp down on the clot 210 during retrieval of the device 1510). In some embodiments in which the device 1510 is formed from a tube, the proximal section 1512 comprises a longitudinal slot to form two edges, and the edges may overlap to form a coiled configuration when viewed from the distal end to enhance interaction with the clot 210 (e.g., by springing open upon release from the catheter 180 and/or by acting as jaws that clamp down on the clot 210 during retrieval of the device 1510). In some embodiments in which the clot 210 is proximate to a bifurcation, the diameter of the distal section 151 may substantially span (e.g., span) the junction of a bifurcation, allowing perfusion to efferent vessels.

FIGS. 22A-22C illustrate example embodiments of proximal sections 222, 224, 226, comprising additional filaments or features that can enhance clot retrieval. FIG. 22A illustrates an example embodiment of a proximal section 222 of a device comprising a plurality of substantially longitudinally straight and radially curved filaments 223 extending between the proximal end of the proximal section 222 and the distal end of the proximal section 222. FIG. 22B illustrates an example embodiment of a proximal section 224 of a device comprising a plurality of spiraled filaments 225 extending between the proximal end of the proximal section 224 and the distal end of the proximal section 224 and/or extending radially outward from the proximal section 224. FIG. 22C illustrates an example embodiment of a proximal section 226 of a device comprising a plurality of substantially longitudinally straight and radially curved filaments 223 extending between the proximal end of the proximal section 226 and the distal end of the proximal section 226 and a plurality of spiraled filaments 225 extending between the proximal end of the proximal section 226 and the distal end of the proximal section 226 and/or extending radially outward from the proximal section 226. FIG. 23 illustrates an example embodiment of a device 230 comprising a distal section 236 comprising a plurality of branches 237. The branches 237 may enhance the capture of stray clots or clot fragments. The branches 237 may also be configured to act as a scaffolding to inhibit herniation of objects out of a neck of a bifurcation aneurysm. As described herein, any combination or permutation of the proximal, intermediate, and distal sections described herein may be used in an intraluminal device for aneurysm treatment, clot retrieval, or other uses.

Although the subject technology has been disclosed in the context of certain embodiments and examples, it will be understood by those skilled in the art that the subject technology extends beyond the specifically disclosed embodiments to other alternative embodiments and/or uses of the subject technology and obvious modifications and equivalents thereof. In addition, while several variations of the embodiments of the subject technology have been shown and described in detail, other modifications, which are within the scope of the subject technology, will be readily apparent to those of skill in the art based upon this disclosure. It is also contemplated that various combinations or sub-combinations of the specific features and aspects of the embodiments may be made and still fall within the scope of the subject technology. It should be understood that various features and aspects of the disclosed embodiments can be combined with, or substituted for, one another in order to form varying modes of the embodiments of the disclosed subject technology. Thus, it is intended that the scope of the subject technology disclosed herein should not be limited by the particular embodiments described above.

What is claimed is:

1. An intraluminal device comprising:
   a proximal section configured to anchor in an afferent vessel;
   an intermediate section comprising a plurality of struts configured to allow perfusion to efferent vessels; and
   a distal section configured to act as a scaffolding to inhibit herniation of objects out of a neck of a bifurcation aneurysm, the distal section forming a circumferentially continuous structure with a plurality of undulating filaments;
   wherein each of the plurality of struts is coupled at a coupling to the distal section at a region between a proximal end of the distal section and a distal end of the distal section;
   wherein the distal section is biased to transition from a first configuration to a second configuration such that the distal end of the distal section moves radially inwardly and retracts proximally relative to the proximal end of the distal section when released from a catheter.

2. The device of claim 1, wherein the proximal section comprises a hybrid cell design comprising open cells and closed cells.

3. The device of claim 1, wherein the proximal section comprises a plurality of repeating unit cells.

4. The device of claim 3, wherein the distal section comprises at least one said unit cell and at least partially forms a semi-sphere, umbrella, or reverse umbrella in an expanded state.

5. The device of claim 1, wherein the proximal section comprises a plurality of woven filaments.

6. The device of claim 1, wherein the proximal section comprises at least one tapered portion.

7. The device of claim 1, wherein the proximal section has a length between about 5 mm and about 30 mm.

8. The device of claim 1, wherein the proximal section has a length between about 10 mm and about 20 mm.

9. The device of claim 1, wherein the intermediate section has a length between about 6 mm and about 10 mm.

10. The device of claim 1, wherein the first configuration forms a cylindrical shape and the second configuration forms a planar shape, and wherein the cylindrical shape has an inner surface and an outer surface, and each of the inner surface and the outer surface of the cylindrical shape define a respective opposing proximal and distal side of the planar shape in the second configuration.

11. The device of claim 1, wherein the distal section has a smallest inner cross-sectional dimension in the second configuration that is less than a smallest inner cross-sectional dimension of the proximal section.

12. The device of claim 1, wherein, while transitioning from the first configuration to the second configuration, the distal end moves to an axial location aligned with the coupling.

13. The device of claim 1, wherein, while transitioning from the first configuration to the second configuration, the proximal end moves to an axial location aligned with the coupling.

14. The device of claim 1, wherein the distal section pivots about the coupling when transitioning from the first configuration to the second configuration.

15. The device of claim 1, wherein, while transitioning from the first configuration to the second configuration, (i) the distal end of the distal section is configured to move radially inwardly and proximally relative to the coupling and (ii) the proximal end of the distal section is configured to move radially outwardly and distally relative to the coupling.

16. The device of claim 15, wherein, while transitioning from the first configuration to the second configuration, the proximal end moves radially outwardly to define, in the second configuration, an outermost cross-sectional dimension that is greater than an outermost cross-sectional dimension of the proximal section.

17. The device of claim 15, wherein, while transitioning from the first configuration to the second configuration, the distal end moves radially inwardly to define, in the second configuration, an innermost cross-sectional dimension that is less than an innermost cross-sectional dimension of the proximal section.

18. The device of claim 15, wherein, when transitioned from the first configuration to the second configuration, the distal end defines a first lumen sized smaller than a second lumen defined by the proximal section.

19. The device of claim 15, wherein the distal section pivots about the coupling when transitioning from the first configuration to the second configuration.

20. The device of claim 1, wherein the undulating filaments are woven.

21. The device of claim 1, wherein the proximal section and the distal section are integrally cut from a tube or a sheet.

22. The device of claim 1, wherein the proximal section and the distal section are comprised of the same material.

23. The device of claim 1, wherein the distal section comprises a covering.

\* \* \* \* \*